US009089600B2

(12) United States Patent
Humayun et al.

(10) Patent No.: US 9,089,600 B2
(45) Date of Patent: Jul. 28, 2015

(54) SYSTEMS AND METHODS FOR IN VITRO AND IN VIVO IMAGING OF CELLS ON A SUBSTRATE

(75) Inventors: Mark Humayun, Glendale, CA (US); Ashish Ahuja, New York, NY (US); Charles Le Pere, Long Beach, CA (US)

(73) Assignees: University of Southern California, Los Angeles, CA (US); Doheny Eye Institute, Los Angeles, CA (US)

( * ) Notice: Subject to any disclaimer, the term of this patent is extended or adjusted under 35 U.S.C. 154(b) by 84 days.

(21) Appl. No.: 14/114,193

(22) PCT Filed: Apr. 27, 2012

(86) PCT No.: PCT/US2012/035671
§ 371 (c)(1),
(2), (4) Date: Oct. 25, 2013

(87) PCT Pub. No.: WO2012/149480
PCT Pub. Date: Nov. 1, 2012

(65) Prior Publication Data
US 2014/0050386 A1    Feb. 20, 2014

Related U.S. Application Data

(60) Provisional application No. 61/481,107, filed on Apr. 29, 2011.

(51) Int. Cl.
*G06K 9/00* (2006.01)
*A61K 49/00* (2006.01)
*A61L 27/38* (2006.01)
*A61F 9/00* (2006.01)

(52) U.S. Cl.
CPC ............. *A61K 49/0017* (2013.01); *A61L 27/38* (2013.01); *A61L 27/3834* (2013.01); *A61F 9/00* (2013.01)

(58) Field of Classification Search
CPC .......... G06K 7/10732; G06K 7/10554; G06K 7/10594
See application file for complete search history.

(56) References Cited

U.S. PATENT DOCUMENTS

| | | | |
|---|---|---|---|
| 4,700,298 A | 10/1987 | Palcic et al. | |
| 8,808,687 B2 | 8/2014 | Humayun et al. | |
| 8,877,489 B2 | 11/2014 | Tai et al. | |
| 2003/0231791 A1 | 12/2003 | De La Torre-Bueno et al. | |
| 2007/0106208 A1 | 5/2007 | Uber, III et al. | |
| 2010/0189338 A1 | 7/2010 | Lin et al. | |
| 2011/0060232 A1 | 3/2011 | Lin et al. | |
| 2012/0009159 A1 | 1/2012 | Humayun et al. | |
| 2013/0144399 A1 | 6/2013 | Tai et al. | |
| 2014/0045264 A1 | 2/2014 | Humayun et al. | |
| 2015/0032207 A1 | 1/2015 | Humayun et al. | |

OTHER PUBLICATIONS

International Search Report and Written Opinion for PCT/US2012/035671, dated Nov. 23, 2012.
International Preliminary Report on Patentability for PCT/US2012/035671, dated Oct. 29, 2013.

*Primary Examiner* — Stephen R Koziol
*Assistant Examiner* — Amandeep Saini
(74) *Attorney, Agent, or Firm* — Knobbe, Martens, Olson & Bear, LLP

(57) ABSTRACT

Disclosed herein are generally to methods and systems that facilitate imaging of cells on a substrate and more particularly to pre-implantation (in vitro) and post-implantation (in vivo) imaging of cell-seeded substrates implanted in target tissues in the context of stem cell therapy.

16 Claims, 22 Drawing Sheets

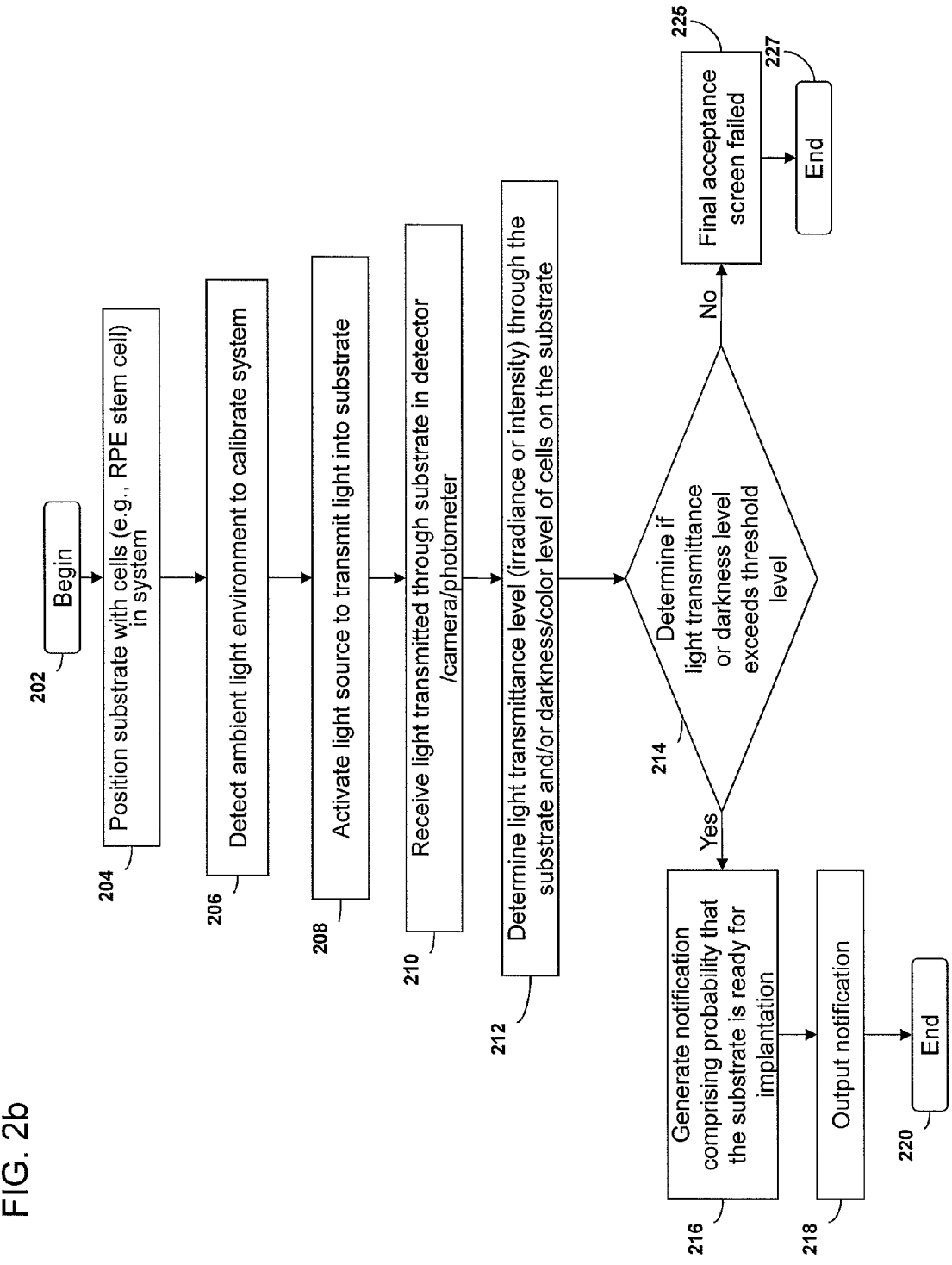

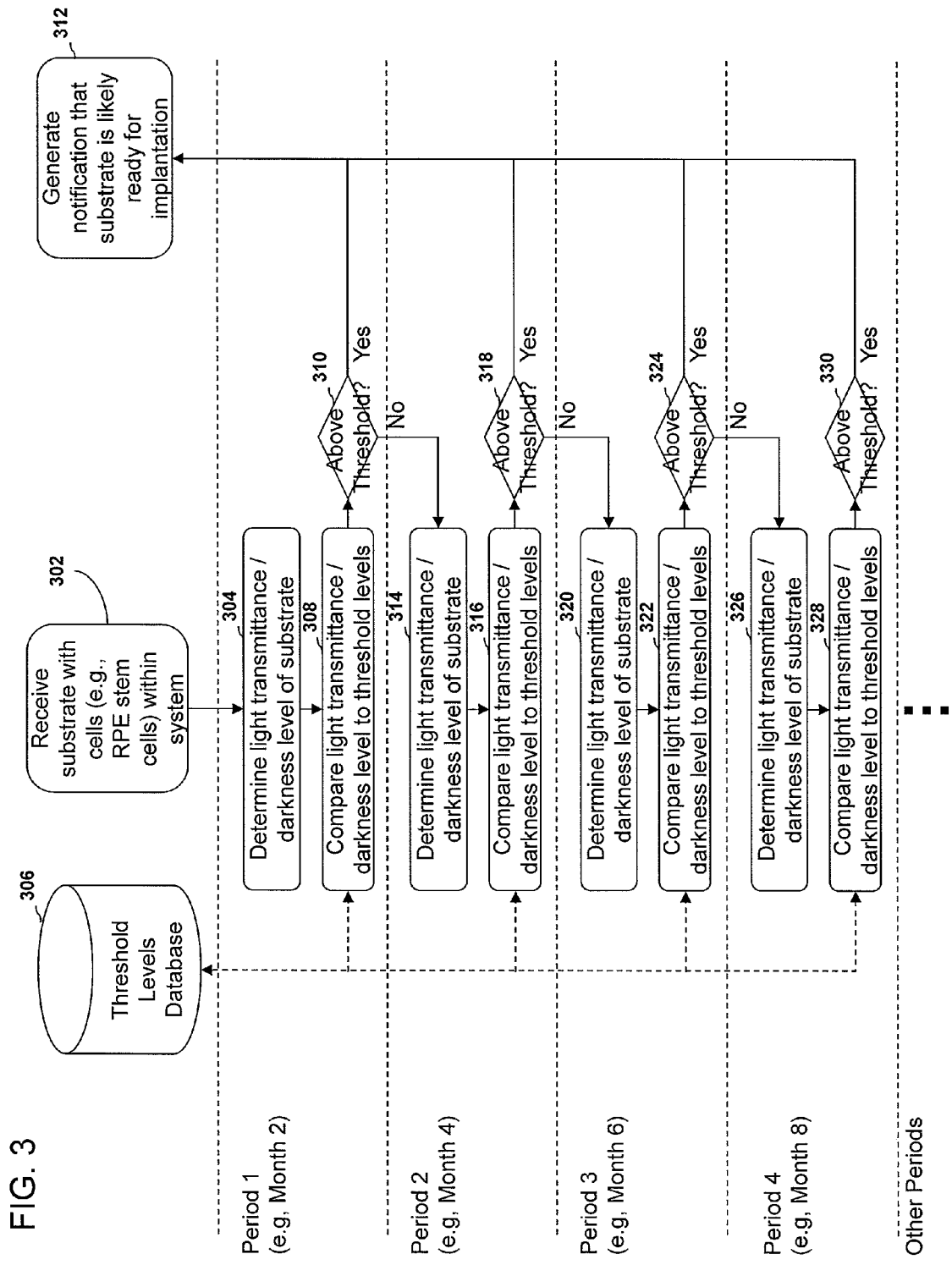

| Lollipop | Number of Cells | | | | |
|---|---|---|---|---|---|
| #1 | 23 | 28 | 30 | 23 | 28 |
| #2 | 30 | 34 | 28 | 28 | 30 |
| #3 | N/A | 28 | 33 | 28 | N/A |
| #4 | 23 | 30 | 31 | 26 | N/A |
| #5 | N/A | 27 | 26 | 25 | 28 |
| #6 | 23 | 26 | 26 | 25 | 28 |

(Average 27.5, STD 6.02)

SYSTEMS AND METHODS FOR IN VITRO AND IN VIVO IMAGING OF CELLS ON A SUBSTRATE

CROSS-REFERENCE TO RELATED APPLICATIONS

This application is the U.S. National Phase application under 35 U.S.C. §371 of International Application No. PCT/US2012/035671, filed Apr. 27, 2012, which claims the benefit of U.S. Provisional Application No. 61/481,107, filed Apr. 29, 2011. Additional non-limiting embodiments of suitable substrates and other systems and methods can be found in United States Provisional Application Nos. 61/363,630, filed Jul. 12, 2010; 61/481,004, filed Apr. 29, 2011; 61/481,037, filed Apr. 29, 2011; 61/481,015, filed Apr. 29, 2011; 61/535,307, filed Sep. 15, 2011, and 61/591,808, filed Jan. 27, 2012. The entirety of each of the foregoing applications is incorporated herein by reference.

BACKGROUND

1. Field

The present application relates generally to methods and systems that facilitate the administration and imaging of cells, and more particularly to facilitate the administration and imaging of stem cells to target tissues in the context of stem cell therapy.

2. Description of the Related Art

The scope of human disease that involves loss of or damage to cells is vast and includes, but is not limited to, ocular disease, neurodegenerative disease, endocrine diseases, cancers, and cardiovascular disease. Cellular therapy involves the use of cells, and in some cases stem cells to treat diseased or damaged tissues. It is rapidly coming to the forefront of technologies that are poised to treat many diseases, in particular those that affect individuals who are non-responsive to traditional pharmacologic therapies.

In fact, many diseases that are candidates for application of cellular therapy are not fatal, but involve loss of normal physiological function. For example, ocular diseases often involve functional degeneration of various ocular tissues which affects the vision, and thus the quality of life of numerous individuals.

The mammalian eye is a specialized sensory organ capable of light reception and is able to receive visual images. The retina of the eye comprises photoreceptors that are sensitive to various levels of light and interneurons that relay signals from the photoreceptors to the retinal ganglion cells, which transmit the light-induced signals to the brain. The iris is an intraocular membrane that is involved in controlling the amount of light reaching the retina. The iris comprises two layers (arranged from anterior to posterior), the pigmented fibrovascular tissue known as a stroma and pigmented epithelial cells. The stroma connects a sphincter muscle (sphincter pupillae), which contracts the pupil, and a set of dilator muscles (dilator pupillae) which open it. The pigmented epithelial cells block light from passing through the iris and thereby restrict light passage to the pupil.

Numerous pathologies can compromise or entirely eliminate an individual's ability to perceive visual images, including trauma to the eye, infection, degeneration, vascular irregularities, and inflammatory problems. The central portion of the retina is known as the macula, which is responsible for central vision, fine visualization and color differentiation. The function of the macula may be adversely affected by age related macular degeneration (wet or dry), diabetic macular edema, idiopathic choroidal neovascularization, high myopia macular degeneration, or advanced retinitis pigmentosa, among other pathologies.

Age related macular degeneration typically causes a loss of vision in the center of the visual field (the macula) because of damage to the retina. It is a major cause of visual impairment in older adults (>50 years). Macular degeneration occurs in "wet" and "dry" forms. In the dry form, cellular debris (drusen) accumulates between the retina and the choroid, which puts pressure on the retina, possibly leading to retinal detachment and loss of vision. In the more severe wet form, newly formed blood vessels from the choroid infiltrate the space behind the macula, which causes death of photoreceptors and their supporting cells. In conjunction with the loss of functional cells in the eye, the newly formed blood vessels are fragile and often leak blood and interstitial fluid, which can further damage the macula.

While diseases that cause damage to specific cells or tissues are clear candidates for cellular therapy, there remains a need in the art for methods and systems to improve the efficacy of cellular therapy by monitoring cells that have been placed on a substrate and monitoring cells implanted into the body.

SUMMARY

Advancements in technology make it possible to determine in vitro whether a substrate comprising stem cell-derived RPE cells is acceptable or ready for implantation to an eye by analyzing using a computer system various metrics. Such metrics can include but are not limited to cell count, cell density, cell-substrate attachment, cell pigmentation, confluence, and light transmittance through the substrate. In addition, it is also possible to monitor and count a number of stem cell-derived RPE cells on a substrate in vivo after implantation in an eye by using a detection device and a computer system. Furthermore, it is also possible to analyze and monitor the functionality of stem cell-derived RPE cells on a substrate in vivo after implantation in an eye according to various metrics. Such metrics can include but are not limited to cell count, cell density, cell-substrate attachment, cell-photoreceptor interdigitation, cell pigmentation, and confluence.

In one embodiment, a computer-implemented method of determining in vitro whether a substrate comprising stem cell-derived RPE cells is acceptable for implantation in an eye comprises directing by a light source light at the substrate; obtaining by a detector an image of the substrate; determining by a computer system a number of stem cell-derived RPE cells on the substrate; determining by the computer system whether the number of stem cell-derived RPE cells is at or above a first pre-stored threshold value; detecting by a detector light transmitted through the substrate; determining by the computer system a light transmittance level; determining by the computer system whether the light transmittance level is at or above a second pre-stored threshold value, wherein the determined light transmittance level indicates pigmentation of the stem cell-derived RPE cells, wherein a certain level of pigmentation of the stem cell-derived RPE cells is an indication of cell functionality sufficient for implantation to the eye; and generating by the computer system a notification that the substrate is acceptable for implantation to the eye based on the determining of whether the number of stem cell-derived RPE cells is at or above the first threshold value and the determining of whether the light transmittance level is at or above the second threshold value, wherein the computer system comprises a computer processor and an electronic storage medium.

In other embodiments, the computer-implemented method can also be repeated over a period of time when the number of stem cell-derived RPE cells is below the first threshold value or the light transmittance level is below the second threshold value. The computer-implemented method can also comprise determining by the computer system an area of confluence between an outer boundary of the substrate and an outer boundary of stem cell-derived RPE cell growth on the substrate; and determining by the computer system whether the area of confluence is at or above a third pre-stored threshold value, wherein the computer system generates the notification that the substrate is acceptable for implantation only when the area of confluence is at or above the third threshold value. The computer-implemented method can also comprise calculating by the computer system a density of stem cell-derived RPE cells on the substrate; and determining by the computer system whether the density of stem cell-derived RPE cells is at or above a fourth pre-stored threshold value, wherein the computer system generates the notification that the substrate is acceptable for implantation only when the density of cells is at or above the fourth threshold value.

In the above computer-implemented methods, the substrate can further comprise markings configured to assist counting a number of stem cell-derived RPE cells. Also in the above computer-implemented methods, the computer system can comprise one or more computer systems. Further, in the above computer-implemented methods, the determining of the light transmittance level can further comprise detecting a level of ambient light and adjusting the determined light transmittance level based on the level of ambient light. In addition, in the above computer-implemented methods, the determining of the light transmittance level further comprises blocking the detector from detecting ambient light by covering the detector with a shield apparatus.

In other embodiments, a computer-implemented method of counting in vivo stem cell-derived RPE cells on a substrate implanted along a curvature of an eye comprises detecting by a detector a plurality of two-dimensional images of the substrate on an x-y plane at a plurality of focal depths along a z axis, wherein the plurality of focal depths comprises a maximum focal depth and a minimum focal depth; identifying by a computer system objects from the plurality of two-dimensional images objects of the substrate that are in focus; mapping by the computer system the identified objects that are in focus from the plurality of two-dimensional images to generate a single image; determining by the computer system a first number of stem cell-derived RPE cells on the substrate; determining double counting of cells by the computer system by identifying stem cell-derived RPE cells appearing at a same x-y coordinate and appearing at different focal depths along the z axis; and determining by the computer system a second number of stem cell-derived RPE cells in the substrate based on the determined number of stem cell-derived RPE cells on the substrate and accounting for the determined double counting of cells, wherein the computer system comprises a computer processor and an electronic storage medium.

In the computer-implemented method above, the maximum focal depth and minimum focal depth can be automatically determined by the computer system. Also, in the computer-implemented method above, the maximum focal depth and minimum focal depth can be manually determined by a user. Further, in the computer-implemented method above, the substrate can further comprise a boundary marker located along edges of the substrate. In other embodiments, the computer-implemented method above can further comprise configuring by the computer system an interval between the plurality of focal depths depending on the pitch of the substrate. In addition, in the computer-implemented method above, an interval between the plurality of focal depths can be about 7 μm. Also, in the computer-implemented method above, the substrate can further comprise highly localized fluorophore markers that are configured to be coupled to the stem cell-derived RPE cells and not to native RPE cells. In addition, in the computer-implemented method above, the determining the first number of the stem cell-derived RPE cells comprises detecting fluorescence emitted from fluorophores coupled to the stem cell-derived RPE cells. Moreover, in the computer-implemented method above, the identifying of double counting of stem cell-derived RPE cells further comprises determining by the computer system whether the stem cell-derived RPE cells appearing at the same x-y coordinate and appearing at different focal depths along the z axis are a single stem cell-derived RPE cell or more than stem cell-derived RPE cell. Furthermore, in the computer-implemented method above, the computer system comprises one or more computer systems.

In other embodiments, a computer-implemented method of analyzing in vivo an implanted substrate comprising stem cell-derived RPE cells comprises directing by a light source narrow-band light at the substrate; detecting by a detector fluorescence that is emitted from fluorophores coupled to the stem cell-derived RPE cells on the substrate; generating by a computer system a plurality of two-dimensional images of the substrate on an x-y plane at a plurality of focal depths along the z axis; combining by the computer system the plurality of two-dimensional images on the x-y plane to generate a single image; determining by the computer system a first number of stem cell-derived RPE cells in the single image; calculating by the computer system a first density of stem cell-derived RPE cells in the single image based on the determined first number of stem cell-derived RPE cells; comparing by the computer system the first number of stem cell-derived RPE cells and the first density of stem cell-derived RPE cells to a second number of stem cell-derived RPE cells and a second density of stem cell-derived RPE cells; and generating by the computer system a report based on the comparing, wherein the computer system comprises a computer processor and an electronic storage medium.

In the computer-implemented method above, the second number of stem cell-derived RPE cells and the second density of stem cell-derived RPE cells can be determined from the same substrate at a second point in time. The computer-implemented method above can further comprise identifying double counting of stem cell-derived RPE cells by the computer system by identifying in-focused objects occurring at a same x-y coordinate and occurring at different focal depths along a z axis. Also, the computer-implemented method above can further comprise employing statistical techniques to approximate a number of cells in non-imaged regions of the substrate. In the computer-implemented method above, the narrow-band light source can have a wavelength of about 488 nm. Also, in the computer-implemented method above, the narrow-band light source can have a wavelength of about 450 nm to about 800 nm. Further, in the computer-implemented method above, the substrate can further comprise markings configured to assist counting a number of stem cell-derived RPE cells. In other embodiments, the computer-implemented method above can further comprise determining a level of interdigitation between stem cell-derived RPE cells on the substrate and photoreceptors.

In other embodiments, the computer-implemented method above can further comprise determining a degree of pigmentation of stem cell-derived RPE cells on the substrate, wherein the determining the degree of pigmentation further comprises directing a first light source at the substrate, wherein the first light source has a wavelength within a range that lipofuscin fluoresces but not melanopsin; generating by the computer system a first image of the substrate from fluorescence reemitted after directing the first light source; counting by the computer system a first number of stem cell-derived RPE cells in the first image; directing a second light source at the substrate, wherein the second light source has a wavelength within a range that melanopsin fluoresces but not lipofuscin; generating by the computer system a second image of the substrate from fluorescence reemitted after directing the second light source; counting by the computer system a second number of stem cell-derived RPE cells in the second image; and comparing by the computer system the first number of stem cell-derived RPE cells to the second number of stem cell-derived RPE cells. In other embodiments, the computer-implemented method above can further comprise determining a degree of spatial separation between the substrate and stem cell-derived RPE cells on the substrate. Also, in the computer-implemented method above, the substrate can further comprise a boundary marker located along edges of the substrate. Further, in the computer-implemented method above, a width of the boundary marker is within a range from about 5 µm to about 500 µm. In addition, in the computer-implemented method above, the computer system can comprise one or more computer systems. In other embodiments, the computer-implemented method above further comprises using photo acoustic imaging to detect a presence of stem cell-derived RPE cells on the substrate. The computer-implemented method above can also further comprise collecting indirect structural information of photoreceptors within the eye by a reflectometer to assess implantation of stem cell-derived RPE cells, wherein the reflectometer is configured to monitor rhodopsin pigment in the photoreceptors. In other embodiments, the computer-implemented method above further comprises collecting indirect structural information of photoreceptors within the eye by adaptive optics with or without a scanning laser opthalmoscope.

In other embodiments, a computer-readable, non-transitory storage medium has a computer program stored thereon for causing a suitably programmed computer system to process by one or more computer processors computer-program code by performing a method when the computer program is executed on the suitably programmed computer system, wherein the method is for determining in vitro whether a substrate comprising stem cell-derived RPE cells is acceptable for implantation in an eye, and wherein the method comprises directing by a light source light at the substrate; obtaining by a detector an image of the substrate; determining by a computer system a number of stem cell-derived RPE cells on the substrate; determining by the computer system whether the number of stem cell-derived RPE cells is at or above a first pre-stored threshold value; detecting by a detector light transmitted through the substrate; determining by the computer system a light transmittance level; determining by the computer system whether the light transmittance level is at or above a second pre-stored threshold value, wherein the determined light transmittance level indicates pigmentation of the stem cell-derived RPE cells, wherein a certain level of pigmentation of the stem cell-derived RPE cells is an indication of cell functionality sufficient for implantation to the eye; and generating by the computer system a notification that the substrate is acceptable for implantation to the eye based on the determining of whether the number of stem cell-derived RPE cells is at or above the first threshold value and the determining of whether the light transmittance level is at or above the second threshold value, wherein the computer system comprises a computer processor and an electronic storage medium.

In other embodiments, a computer-readable, non-transitory storage medium has a computer program stored thereon for causing a suitably programmed computer system to process by one or more computer processors computer-program code by performing a method when the computer program is executed on the suitably programmed computer system, wherein the method is for counting in vivo stem cell-derived RPE cells on a substrate implanted along a curvature of an eye, and wherein the method comprises detecting by a detector a plurality of two-dimensional images of the substrate on an x-y plane at a plurality of focal depths along a z axis, wherein the plurality of focal depths comprises a maximum focal depth and a minimum focal depth; identifying by a computer system objects from the plurality of two-dimensional images objects of the substrate that are in focus; mapping by the computer system the identified objects that are in focus from the plurality of two-dimensional images to generate a single image; determining by the computer system a first number of stem cell-derived RPE cells on the substrate; determining double counting of cells by the computer system by identifying stem cell-derived RPE cells appearing at a same x-y coordinate and appearing at different focal depths along the z axis; and determining by the computer system a second number of stem cell-derived RPE cells in the substrate based on the determined first number of stem cell-derived RPE cells on the substrate and accounting for the determined double counting of cells, wherein the computer system comprises a computer processor and an electronic storage medium.

In other embodiments, a computer-readable, non-transitory storage medium has a computer program stored thereon for causing a suitably programmed computer system to process by one or more computer processors computer-program code by performing a method when the computer program is executed on the suitably programmed computer system, wherein the method is for analyzing in vivo an implanted substrate comprising stem cell-derived RPE cells, and wherein the method comprises directing by a light source narrow-band light at the substrate; detecting by a detector fluorescence that is emitted from fluorophores coupled to the stem cell-derived RPE cells on the substrate; generating by a computer system a plurality of two-dimensional images of the substrate on an x-y plane at a plurality of focal depths along the z axis; combining by the computer system the plurality of two-dimensional images on the x-y plane to generate a single image; determining by the computer system a first number of stem cell-derived RPE cells in the single image; calculating by the computer system a first density of stem cell-derived RPE cells in the single image based on the determined first number of stem cell-derived RPE cells; comparing by the computer system the first number of stem cell-derived RPE cells and the first density of stem cell-derived RPE cells to a second number of stem cell-derived RPE cells and a second density of stem cell-derived RPE cells; and generating by the computer system a report based on the comparing, wherein the computer system comprises a computer processor and an electronic storage medium.

In other embodiments, a system for determining in vitro whether a substrate comprising stem cell-derived RPE cells is acceptable for implantation in an eye comprises a light source configured to direct light at a substrate; a detector configured to obtain an image of the substrate and to detect light transmitted through the substrate; and a storage computer system comprising a computer processor configured to execute modules comprising at least a cell counting module programmed to determine a number of stem cell-derived RPE cells on the substrate; a cell count analysis module programmed to determine whether the number of stem cell-derived RPE cells is at or above a first pre-stored threshold value; a light transmission determination module programmed to determine a light transmittance level through the substrate; a light transmission analysis module programmed to determine whether the light transmittance level is at or above a second pre-stored threshold value, wherein the determined light transmittance level indicates pigmentation of the stem cell-derived RPE cells, and wherein a certain level of pigmentation of the stem cell-derived RPE cells is an indication of cell functionality sufficient for implantation to the eye; and a notification module programmed to generate a notification that the substrate is acceptable for implantation to the eye based on the determining of whether the number of stem cell-derived RPE cells is at or above the first threshold value and the determining of whether the light transmittance level is at or above the second threshold value.

In other embodiments, a system for counting in vivo stem cell-derived RPE cells on a substrate implanted along a curvature of an eye comprises a detector configured to detect a plurality of two-dimensional images of the substrate on an x-y plane at a plurality of focal depths along a z axis, wherein the plurality of focal depths comprises a maximum focal depth and a minimum focal depth; and a storage computer system comprising a computer processor configured to execute modules comprising at least an object identification module programmed to identify objects from the plurality of two-dimensional images objects of the substrate that are in focus; a mapping module programmed to map the identified objects that are in focus from the plurality of two-dimensional images to generate a single image; an initial cell counting module programmed to determine a first number of stem cell-derived RPE cells on the substrate; a double cell counting identification module programmed to determine double counting of cells by the computer system by identifying stem cell-derived RPE cells appearing at a same x-y coordinate and appearing at different focal depths along the z axis; and a final cell counting module programmed to determine a final number of stem cell-derived RPE cells in the substrate based on the determined first number of stem cell-derived RPE cells on the substrate and accounting for the determined double counting of cells.

In other embodiments, a system for analyzing in vivo an implanted substrate comprising stem cell-derived RPE cells comprises a light source configured to direct a narrow-band light at the substrate; a detector configured to detect fluorescence that is emitted from fluorophores coupled to the stem cell-derived RPE cells on the substrate; and a storage computer system comprising a computer processor configured to execute modules comprising at least an image generating module programmed to generate a plurality of two-dimensional images of the substrate on an x-y plane at a plurality of focal depths along the z axis; an image stitching module programmed to combine the plurality of two-dimensional images on the x-y plane to generate a single image; a cell counting module programmed to determine a first number of stem cell-derived RPE cells in the single image; a cell density calculation module programmed to calculate a first density of stem cell-derived RPE cells in the single image based on the determined first number of stem cell-derived RPE cells; an analysis module programmed to compare the first number of stem cell-derived RPE cells and the first density of stem cell-derived RPE cells to a second number of stem cell-derived RPE cells and a second density of stem cell-derived RPE cells; and a report generation module programmed to generate a report based on the comparing.

For purposes of this summary, certain aspects, advantages, and novel features are described herein. It is to be understood that not necessarily all such advantages may be achieved in accordance with any particular embodiment. Thus, for example, those skilled in the art will recognize that the invention may be embodied or carried out in a manner that achieves one advantage or group of advantages as taught herein without necessarily achieving other advantages as may be taught or suggested herein.

BRIEF DESCRIPTION OF THE DRAWINGS

The systems and methods disclosed herein and other features, aspects and advantages of the embodiments of the invention are described in detail below with reference to the drawings of various embodiments, which are intended to illustrate and not to limit the invention. The drawings comprise the following figures in which:

FIG. 2B is a flow chart depicting an embodiment of an in vitro substrate verification testing without a feedback loop.

FIG. 3 is a flow chart depicting an embodiment of an in vitro substrate verification testing performed over a plurality of periods.

DETAILED DESCRIPTION

Figure 1:
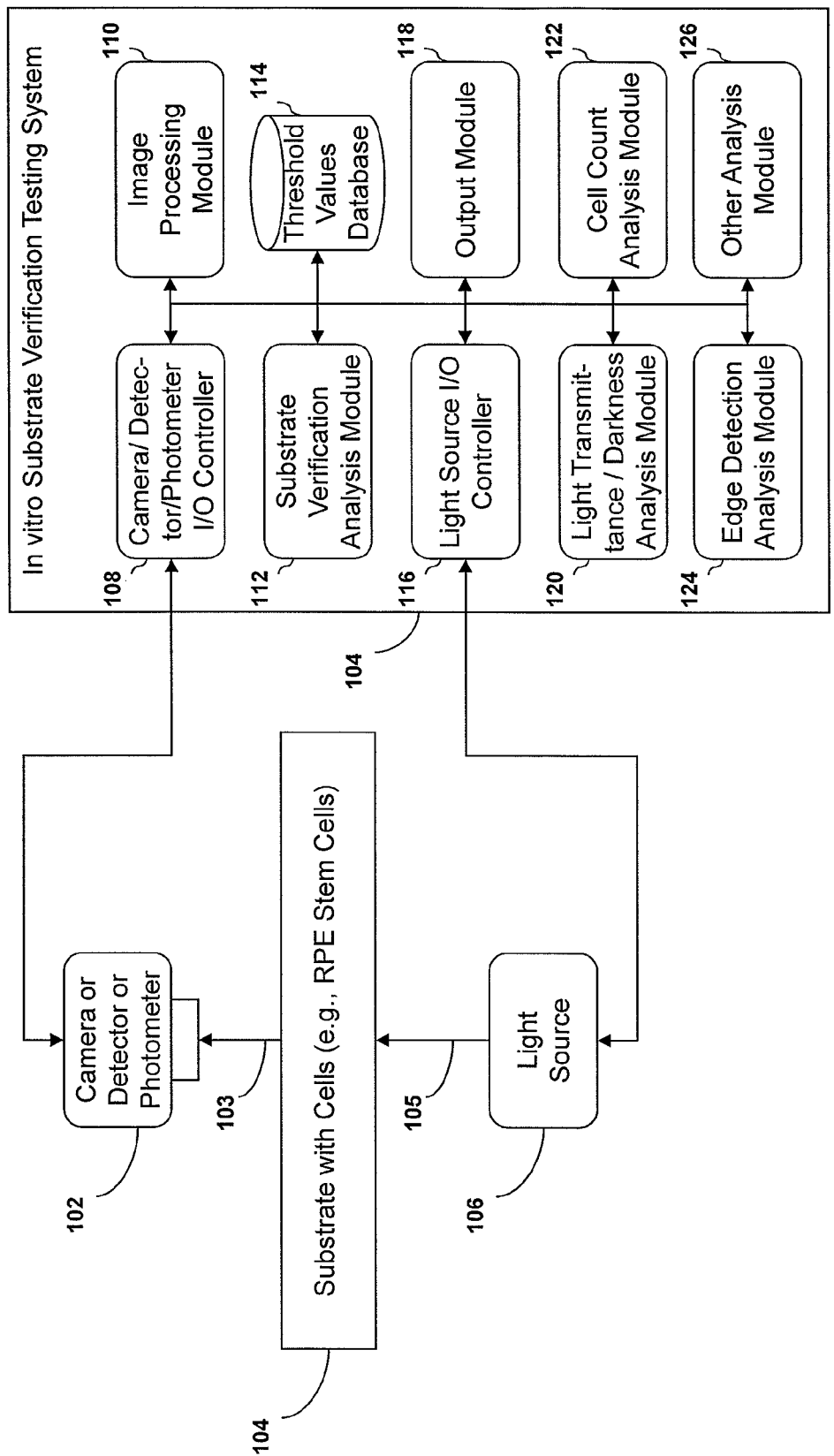
FIG. 1 is a schematic diagram illustrating an embodiment of an in vitro substrate verification testing system.

The system and methods disclosed herein generally describe imaging methodologies for tracking cells, for example, stem cells, before and after implantation to identify the location of the cells and/or to quantify the functionality of the cells on a substrate, for example, a polymeric substrate. The systems and method disclosed herein can be particularly useful for in vitro and/or in vivo quantification and/or localization of hESC-RPE stem cells on or within a substrate.

In the utilization of cells for therapeutic treatments, in particular the use of stem cells positioned on and/or within an implantable substrate, there can be at least two concerns: 1. quantifying and/or tracking cells positioned on and/or within the substrate prior to implantation to determine whether the cells are ready and/or adequate and/or safe for implantation; 2. quantifying and/or tracking cells positioned on and/or within the substrate after the substrate has been implanted into a patient.

With respect to the first concern about quantifying and tracking cells on the substrate prior to implantation, there can be a need to determine the following information relating to the cells on and/or within the substrate: cell growth, cell count, cell location, cell quality, cell type, cell abnormalities, and the like. For example, if a substrate comprises cells that exhibit abnormal cell growth, then the cells on the substrate are not likely to survive implantation and/or may not provide a therapeutic result or there may be concerns about the safety and/or efficacy of the cells. Accordingly, abnormal cell growth may indicate that the cells and the substrate should not be implanted and should be discarded. Similarly, if the cell count, cell location, cell quality, cell type, and the like are below certain threshold levels, then the substrate may not be a good candidate or product for implantation.

There can also be a need to ensure that the cells are properly oriented on the substrate. For example, RPE stem cells must be oriented in a certain direction to receive light through the iris otherwise the RPE stem cells may not properly function. Accordingly, the systems and methods disclosed herein describe various embodiments for performing in vitro analysis and/or imaging of cells, for example, RPE stem cells, on a substrate.

With respect to the second concern about quantifying and tracking cells on and/or within a substrate after implantation, there can be a need to determine whether the cells in vivo are growing, multiplying, functioning, properly oriented or arranged, not migrating off the substrate and into other areas, not differentiating into other types of cells, and the like. Additionally, there can be a need to reliably compare the in vivo data measurements relating to the cells on and/or within the substrate to the in vitro data measurement baselines obtained prior to implantation. For example, generally there is relatively minimal clinical data relating to implanted hESC-derived stem cells. Accordingly, there can be legitimate concerns about the potential for differentiated stem cells to become cancerous or transdifferentiate into biologically inappropriate cell types. In addition, there are efficacy concerns about the ability for the differentiated stem cells to retain their therapeutic properties post-implantation. Accordingly, the systems and methods disclosed herein describe various embodiments for performing in vivo analysis and/or imaging of cells, for example, RPE stem cells, on a substrate.

Generally, in vivo imaging can be invaluable in assessing both the safety and efficacy of the stem cell therapy through analyzing the number of cells and their relative locations with respect to the implanted substrate, and assessing if hESC-RPE cells are differentiating into other cell types, including non-functional RPE-like cells. A substrate can be optimized by incorporating unique markers and data points for the analysis of the cells, for example, hESC-RPE cells.

In generating images for in vivo image analysis, it can be advantageous for the system to "stitch" and/or combine together multiple images obtained at different focal depths to create a single, three-dimensional representation or image of the retina and the implanted substrate with cells. After generating a three-dimensional representation or image, it can be advantageous for the system to be configured to apply biological rules and/or algorithms to the stitched image to accurately quantify the number (and, for example, account for double counting of cells), the location, and the expression of the cells, for example, hESC-RPE cells.

Generally, in order to show efficacy of the cells and/or the substrate, the image data and analysis can be summarized in five key metrics: cell count, cell density, cell-to-substrate attachment; cell interdigitation; and cell pigmentation. Other metrics may be possible. Assessment of the metrics in vitro and in vivo over time will demonstrate stem cell, for example, hESC-RPE stem cells, viability, functionality, and health.

In Vitro Imaging

The systems and methods disclosed herein can be configured to perform cell counts can be performed repeatedly on seeded substrates before implantation using an optical microscope. Based on current optical observations performed manually, substrates, having a dimension of approximately 0.4 mm×0.9 mm, comprise seeding density of approximately $6.2 \times 10^3$ cells/mm$^2$ (SE is ±2%; n=6 substrates sampled at 3 locations each). These optical cell counts can serve as a baseline assessment of dose delivered by the implant.

As discussed above, the in vitro imaging can be used to determine whether a substrate is ready for implantation, or has satisfied certain threshold levels during quality control testing, also referred to as release testing, while the substrate is in a clinical assay that precedes placing the substrate (also referred to as a medical device or drug) in vivo. Generally, in order for the therapeutic (i.e., the substrate) to pass the release testing, the substrate must meet a predetermined criteria or pass one or more threshold levels. One or more of the aforementioned metrics (for example, a minimum cell count and density) can be incorporated into the release testing process.

In Vivo Imaging

Fundus Autofluorescence (FAF)

Figure 14:
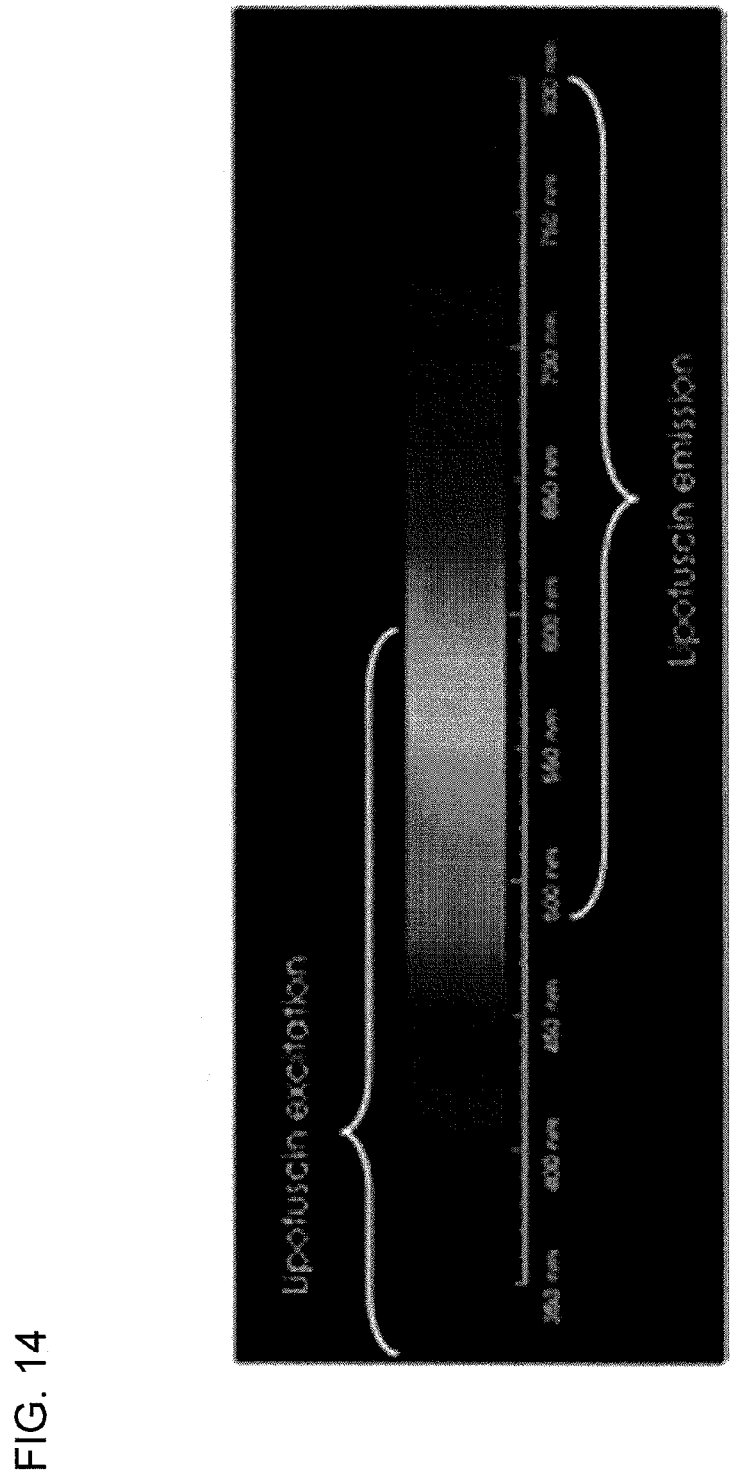
FIG. 14 illustrates lipofuscin excitation and emission ranges.

Two-dimensional images of implanted hESC-RPE cells can be obtained using a commercially available infrared fundus autofluorescence (FAF) confocal scanning laser ophthalmoscope (cSLO) (for example, but not limited to, the Spectralis HRA-OCT manufactured by Heidelberg Engineering, Inc.). In FAF imaging, a narrow-band light source excites associated fluorophores in the retina causing them to emit radiation of particular frequencies. This is generally known as fluorescing. Based on different excitation frequencies, different cells may fluoresce at different frequencies. In healthy RPE cells both lipofuscin and melanopsin fluoresce when excited by a narrowband light source of wavelength of about 488 nm. The fluorescent radiation can be captured using the cSLO and optical band-pass filtering. Typically, lipofuscin and melanopsin fluoresce in wavelength ranges of 450-800 nm. FIG. 14 shows lipofuscin excitation and emission ranges.

RPE Markers Embedded into Substrate

Using imaging to isolate the implanted hESC-RPE cells from the patient's native RPE cells can be challenging, especially because the retina is curved. To ease quantification of the hESC-RPE cell counts in vivo, the substrate can be implanted with highly localized fluorophore markers. This will help differentiate between hESC-RPE cells and native RPE cells. Introducing specific marking agents to the retina can cause RPE cells to fluoresce at specific wavelengths which can then be imaged by applying specific band-pass filters to various imaging instruments akin to FAF imaging described above.

Other Imaging Techniques

An additional method of determining whether seeded hESC-RPE cells are attached to the substrate involves designing the polymeric substrate using a material with specific indices of refraction and birefringence. The advantage of this method is that it does not require cell counting before and after implantation or the use and development of custom algorithms.

This method employs either phase-contrast microscopy or a set of polarization filters coupled with standard light microscope set-ups to determine areas of the substrate surface left bare due to lack of RPE cells because of migration or shear force imparted during implantation.

Image Stitching

Due to the confocal capabilities of cSLO, images can be taken at different depths within the retina (i.e., in the z-direction). This capability can be advantageous since the hESC-RPE cells are implanted in the posterior pole, which is generally a curved surface. Imaging all of the implanted hESC-RPE cells is not always possible without a confocal system since cells may be located in different depths or different focal planes from one another. The methods and system disclosed herein can be configured to use algorithms to stitch together or combine the FAF cross-sectional images (square or rectangular areas in the x-y direction) to create a three-dimensional tomographic image of the retina and implant.

Stitching together or combining several 2D images to create a 3D map of the implant can require storing the 2D images in a 3D array based on the focal depth of each image. A map of the implant will be computer generated and/or superimposed using the known dimensions of the substrate and through the use of identified metal markers that may be imbedded into the substrate. System can be configured to employ filters and/or image processing techniques to be applied to each 2D image identifying which regions of the photo are in focus. Each of these regions can be weighted according to their perceived focus. The substrate and implanted cells can be mapped back to a flat 2D surface utilizing a unique scheme to give imaging priority to regions that were weighted higher for their focus than others.

Analysis

The system can be configured to use biological rules based on anatomical and morphological data to identify the number, location, and expression of the hESC-RPE. The system can be configured to examine a plurality of metrics including but not limited to:

i) Cell Count

Cell count can be a useful metric for in vitro and/or in vivo image analysis. The ability to define the boundaries of individual cells and to differentiate between cells and surrounding biotic and abiotic material, such as drusen and the substrate, can be crucial to analyzing the medical impact of hESC-RPE cells over time because medical benefit is highly correlated with the number of hESC-RPE cells implanted into the retina.

In order to visually identify the hESC-RPE cells through an automated software program, the system can be configured to employ specific forms of image contrast correlated with the hESC-RPE cells to compare to biological criteria for RPE cells. For example, calculated cell criteria such as center-to-center spacing, cell pitch, and circumferential length will be compared to pre-determined minimum and maximum thresholds. In addition, the system can be configured to account for double counting of cells by using geometrical analysis routines that spatially locate cells in a 3-dimensional space, for example, in a radial grid.

Cell counts can be calculated for the substrate as a whole and for specific subsections of the substrate. If certain areas of the substrate cannot be properly imaged, statistical techniques can be used to approximate the cell count in the non-imaged regions.

ii) Cell Density

After calculating a cell count, the system can be configured to calculate cell density for the entire substrate and/or for specific subsections of the substrate. Variation between the global density and local densities can be analyzed by the system through variance metrics such as standard deviation.

In general, the therapeutic benefit of hESC-RPE on the photoreceptors requires a minimal level of cell density. Tracking variation in cell densities across the substrate can allow analysis of both hESC-RPE "fallout"—regions with significantly less hESC-RPE density than surrounding areas—and "reduction"—even loss of hESC-RPE cells across the entire substrate.

iii) Cell-Substrate Attachment

RPE cells are epithelial. As a result, proper functional expression requires attachment to a surface, e.g., native RPE cells lining the Bruch's membrane. While cell count and density alone can be indicative of the relative functioning of the hESC-RPE cells, it can be misleading to count hESC-RPE cells that have detached from the substrate because such cells may likely have a lesser therapeutic effect.

In order to differentiate between attached and detached RPE cells the stitched or combined 3D map can be used by the system. If there is a spatial separation between the fluorescing cell and the substrate, then the system can identify and/or tag the cell with an approximated separation distance. To further emphasize the substrate surface from the hESC-RPE cells, further imaging techniques may be utilized by the system.

iv) RPE-Photoreceptor Interdigitation

Native RPE cells interdigitate with the photoreceptors in order to provide tighter junctions with photoreceptors and improve the exchange of chemicals. Interdigitation is a strong indicator that the hESC-RPE cells have integrated effectively with the photoreceptors. In order to assess interdigitation between the native photoreceptors and implanted hESC-RPE cells, the system can be configured to utilize the stitched 3D map.

v) Cell Pigmentation (Melanopsin)

Native RPE cells are darkly pigmented. Healthy and properly functioning hESC-RPE cells will also typically be pigmented. In order to assess the degree of hESC-RPE cell pigmentation, the system can be configured to compare two FAF images: one image using the lipofuscin emission range and the second image using the melanopsin emission range. Given that melanopsin, but not lipofuscin, is highly correlated with cell pigmentation, if the system detects or identifies a cell on the lipofuscin image but not on the melanopsin image, then the system can be configured to determine that the cell is not pigmented. This two-step pigmentation analysis can allow the aforementioned metrics to be run with the additional criteria of pigmentation, e.g., total cell count vs. pigmented cell count.

c) Efficacy Assessment

The system can be configured to perform comparisons between the in vitro and in vivo metrics to conduct biological assessments of efficacy that can be correlated with behavioral determinations of efficacy, e.g., visual acuity in the patient. In addition, tracking the metrics over time can allow for iterative improvements in the methodologies and materials for substrate development, hESC-RPE seeding, and transplantation. For example, if cell count remains high immediately post-implantation but cell density variation increases significantly this could suggest that certain regions of the substrate are subject to excessive forces that are causing non-uniform fall-out of hESC-RPE cells.

Although several embodiments, examples and illustrations are disclosed below, it will be understood by those of ordinary skill in the art that the invention described herein extends beyond the specifically disclosed embodiments, examples and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the invention. In addition, embodiments of the invention can comprise several novel features and no single feature is solely responsible for its desirable attributes or is essential to practicing the inventions herein described.

FIG. 1 is a block diagram illustrating an embodiment of an in vitro substrate verification testing system. As discussed above, the system can be used to determine whether the cells on and/or within a substrate, or whether the substrate, is acceptable or ready for implantation into a patient.

The in vitro substrate verification testing system can comprise a camera system 102. As used herein, the term "camera" is a broad term, and can be used herein interchangeably with "detector" and "photometer", and unless otherwise indicated, these terms can include within their meaning, without limitation, cameras, detectors, photometers, sensors, and the like for detecting and/or measuring lumens and or radiants. An example of a camera that can be used includes but is not limited to Spectralis HRA-OCT manufactured by Heidelberg Engineering, Inc.; however, other cameras, detectors, sensors, and/or photometers can be used. The in vitro substrate verification testing system can also comprise a light source 106. In an embodiment the light source 106 can be configured to shine light through a substrate 104 comprising cells. Depending on the substrate and the number of cells growing on or within the substrate, light rays 105 generated by light source 106 can be transmitted through substrate 104 as a reduced light stream 103 that can be detected by the camera 102.

In an embodiment the camera can be configured to detect the light stream 103 and output a signal to the camera input-output controller 104 of the in vitro substrate verification testing system. The data relating to the light stream 103 can be processed by various modules in the in vitro substrate verification testing system. For example, the image processing module 110 can be configured to generate an image based on the data relating to the light stream 103. In an embodiment, the image processing module can be configured to generate an enhanced image based on the data.

The data generated by the camera 102 can also be processed by the substrate verification analysis module 112. The substrate verification analysis module 112 can be configured to interact with other components of the in vitro substrate verification testing system. For example, the substrate verification analysis module 112 can compare the data values with stored threshold values in the database 114. The substrate verification analysis module 112 can also interact with the light transmittance/darkness analysis module 120 to analyze the data to determine the level of light transmittance through the substrate or the darkness level of the cells on or within the substrate.

The substrate verification analysis module 112 can also be configured to interact with cell count analysis module 122 to determine the number of cells within or on substrate 104. Alternatively, the substrate verification analysis module 112 can be configured to interact with edge detection analysis module 124 to measure cell growth based on boundary detection analysis. The substrate verification analysis module 112 can also be configured to interact with other analysis modules 126.

Figure 1B:
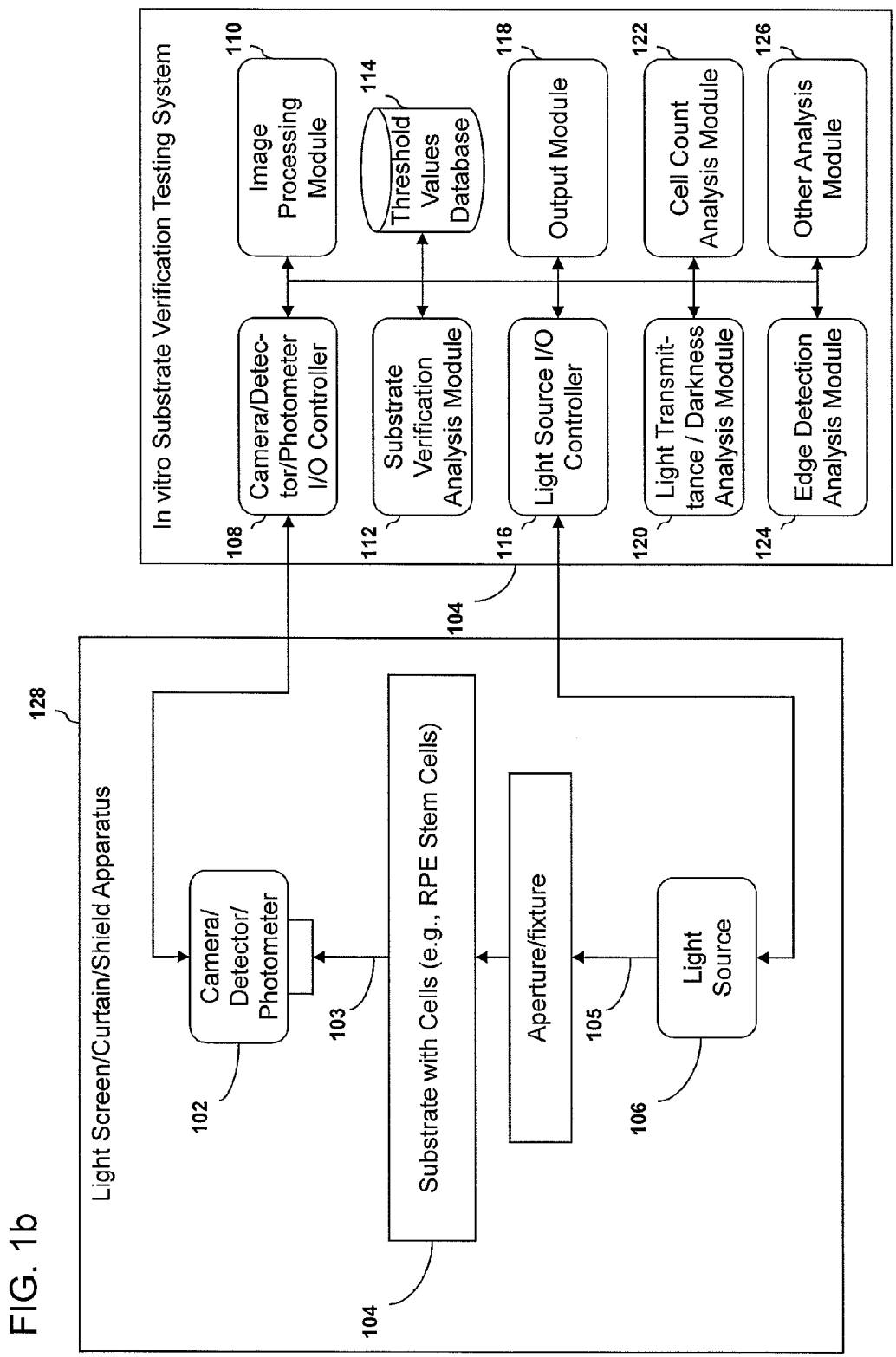
FIG. 1B is a schematic diagram illustrating an embodiment of an in vitro substrate verification testing system having a light screen or curtain or shield apparatus.

As illustrated in FIG. 1B, the in vitro substrate verification testing system can also comprise a light screen or a curtain or shield apparatus to remove or substantially remove ambient light in order for the camera to obtain clean data. Alternatively, the in vitro substrate verification testing system can be configured to detect ambient light and subtract the ambient light form the data obtained from camera 102. In an embodiment, it can be advantageous to use a light screen or a curtain or shield as illustrated in FIG. 1B to reduce the processing power and/or time necessary when subtracting out ambient light from the data obtained from camera 102. Additionally, there may be less data loss when using a light screen or curtain or shield apparatus 128. In an embodiment the system can comprise both a light screen or a curtain or shield in addition to a process for subtracting ambient light from the data detected by the camera 102.

Figure 2:
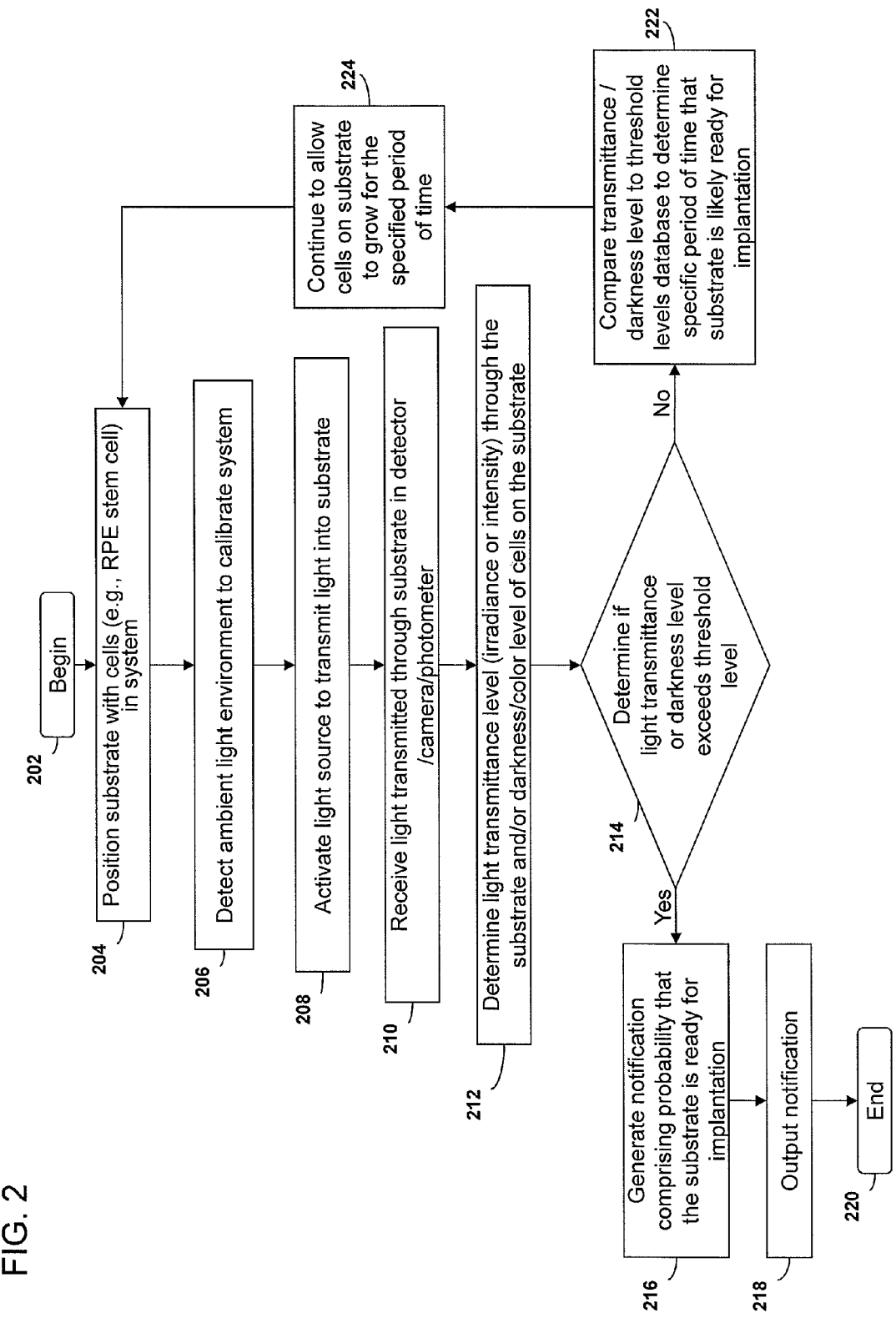
FIG. 2 is a flow chart depicting an embodiment of a process for in vitro substrate verification testing.

FIG. 2 is a flow chart depicting an embodiment of a process for determining light transmittance levels through a substrate. The process can begin at block 202 wherein a substrate can be positioned in the system at block 204. The substrate comprising cells, for example RPE stem cells, can be positioned within or under or on top the system in a variety of different ways. As illustrated in FIGS. 1 and 1B, the substrate can be positioned on top of the light source 106. Optionally, the substrate can be positioned in a system such that the substrate resides within a shielded area that prevents ambient light from interfering with the detection process.

At block 206, the system can be configured to detect ambient light in the surrounding environment to calibrate the system. This calibration will allow the system to subtract out the ambient light when analyzing the substrate. At block 208, the system can activate the light source 106 to transmit light into the substrate. At block 210, the system can receive light transmitted through the substrate in the camera 102. At block 212, the system can be configured to determine the light transmittance level, for example, irradiance or intensity, through the substrate. Alternatively, the system can be configured at block 212 to determine the darkness and/or the color level of the cells positioned within or on the substrate.

At decision block 214, the system can be configured to determine if the detected light transmittance or darkness level exceeds a threshold level. If the detected levels exceed the threshold level, the system at block 216 can be configured to generate a notification. The notification to a user can comprise a probability that the substrate is ready for possible implantation. Alternatively, the notification can indicate that the substrate comprises an adequate number of cells as required by a government entity or other quality control measure. At block 218 the system can be configured to output the notification and end the process at block 220. Alternatively, if the detected level is below the threshold level at decision block 214, the system at block 222 can be configured to compare the transmittance or darkness level to other threshold levels stored in a threshold levels database 114 to determine a specific period of time that the substrate is likely to be ready for implantation or other use.

At block 224, the system can be configured to allow the cells within or on the substrate to grow for the specified period of time determined at block 222. In an embodiment, the system can be configured to repeat the process of analyzing the substrate by repositioning the substrate within the system at block 204.

FIG. 2B is a flow chart similar to that of FIG. 2 except that in an embodiment the system does not allow for the cells to continue to grow on or within the substrate. Rather, at block 225 in FIG. 2B the system ends the process if the detected transmittance or darkness level fails to exceed a threshold level. In an embodiment, if the substrate fails to pass the transmittance or darkness level threshold levels, the substrate may be discarded.

FIG. 3 is a flow chart that illustrates a process for applying the in vitro substrate verification testing system over a plurality of periods to determine the readiness of a substrate for implantation. In an embodiment the process can begin at block 302 by receiving or accessing a substrate comprising cells, for example RPE stem cells by the system. At block 304 the system can be configured to determine the light transmittance or darkness level of the substrate. At block 308 the system can be configured to compare the detected light transmittance or darkness level to threshold levels stored in thresholds levels database 306. At decision block 310 the system determines whether the light transmittance or darkness level exceeds the threshold. If the detected level exceeds the threshold, then the system can be configured to generate a notification that the substrate is likely ready for implantation at block 312. If the system determines at block 310 that the detected levels are below a threshold level then the system can be configured to allow the cells on or within the substrate to continue growing for a period of time, for example, period 2. At the end of period 2, the system can be configured at block 314 to determine the light transmittance and/or the darkness level of the substrate. At block 316, the system can be configured to compare the light transmittance and/or the darkness level to threshold levels. At block 318 the system can be configured to determine if the detected levels exceed a threshold level. If the detected levels do exceed a threshold level, then the system can be configured to output and/or generate at block 312 a notification that the substrate is likely ready for implantation. If the detected levels are below a threshold level, then the system can be configured to allow the cells within or on the substrate to grow for another period, for example, period 3.

At block 320, the system can be configured to determine the light transmittance or the darkness level of the substrate. At block 322, the system compares the light transmittance and/or the darkness level to a threshold level. At decision blocks 324, if the detected levels are above a threshold level, the system can be configured to generate or output a notification that the substrate is likely ready for implantation at block 312. If the system determines that the detected levels are below a threshold level, the system can be configured to allow the cells on or within the substrate to grow for another period of time, for example, period 4. At the end of period 4, the system can be configured at block 326 to determine the light transmittance and/or the darkness level of the substrate. At block 328, the system compares the light transmittance and/or the darkness level to threshold levels. If the system determines that the detected levels are above a threshold level, then the system can be configured to generate or output a notification that the substrate is likely ready for implantation at block 312.

If the system determines that the detected levels are below a threshold level, the system can be configured to allow the cells to continue to grow for yet another period. Alternatively, the system can be configured to tag or identify the substrate for destruction or to be discarded if the detected light transmittance or darkness level of the substrate does not reach a specified or desired threshold level within a certain period or periods of time.

Figure 3B:
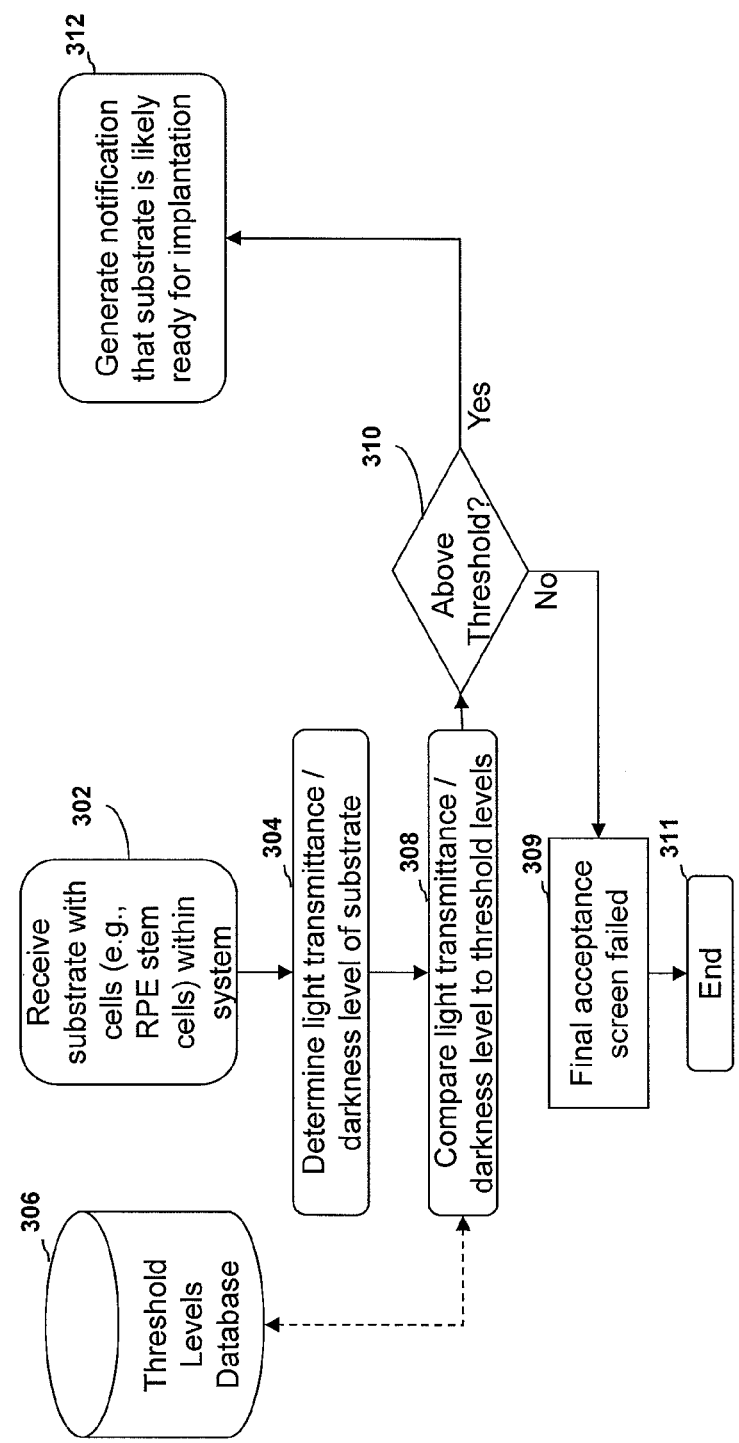
FIG. 3B is a flow chart depicting an embodiment of an in vitro substrate verification testing occurring over a single period.

FIG. 3B is a flow chart illustrating a process that is similar to the process illustrated in FIG. 3 except the process illustrated in FIG. 3B only occurs for one period. In an embodiment, the system can be configured to determine the light transmittance and darkness level of the substrate and compare the detected levels to a threshold level. If the detected level is above a threshold level, the system can be configured to generate a notification that the substrate is likely ready for implantation. If the detected level is below a threshold level, then the system can be configured to identify the substrate as having failed a final acceptance screen at block 309 as illustrated in FIG. 3B, at which point the process ends at block 311. If the substrate fails the final acceptance screen, the system can be configured to tag or identify the substrate for destruction or to be discarded.

Figure 4:
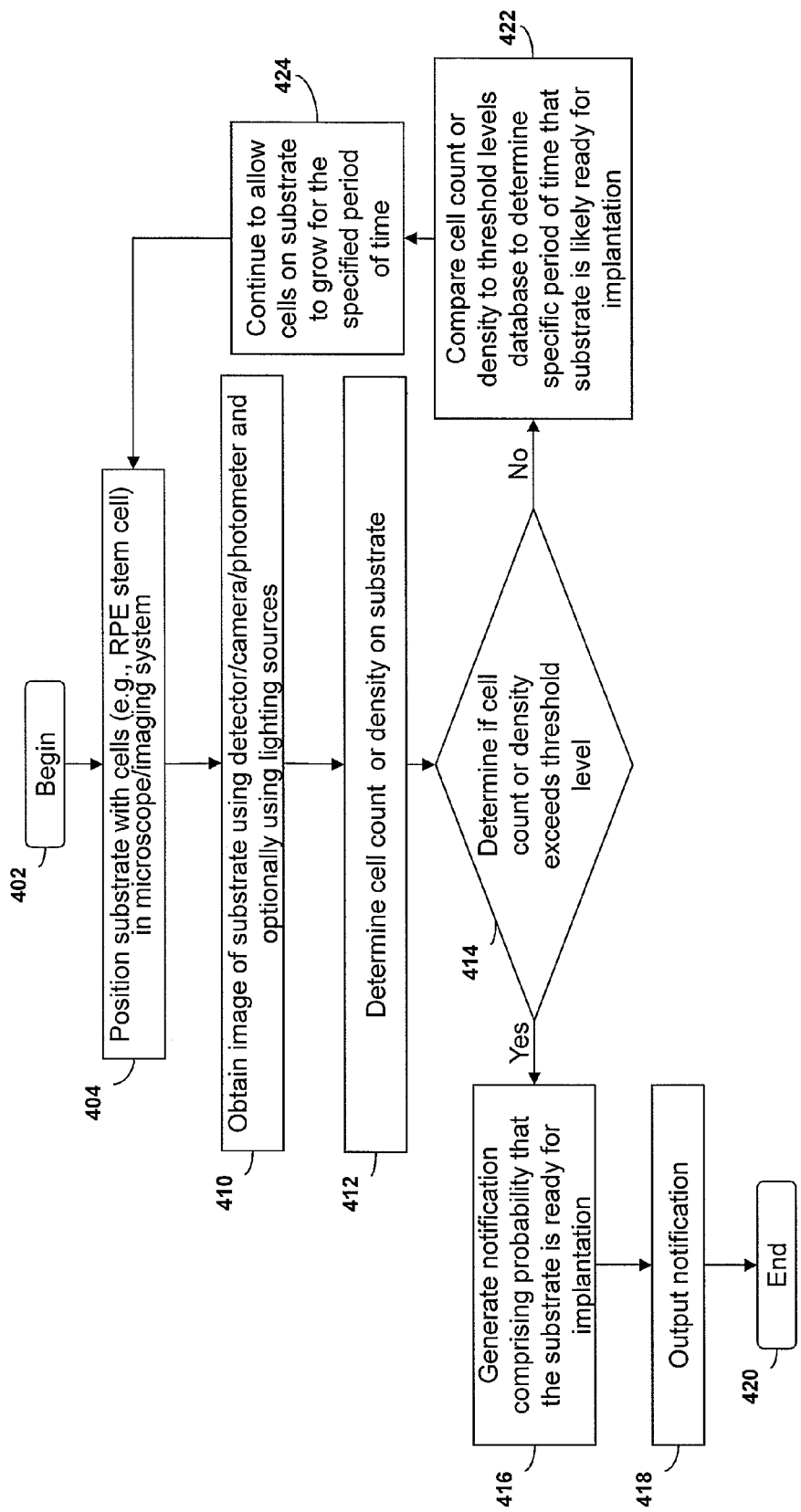
FIG. 4 is a flow chart depicting an embodiment of an in vitro substrate verification testing based on cell count.

FIG. 4 is a flow chart illustrating a process for using cell count or cell density to determine whether a substrate is ready for implantation. In an embodiment, the process can begin at block 402 where the substrate comprising cells, for example RPE stem cells, is positioned in or under a microscope or other imaging system at block 404. At block 410, the system can be configured to obtain an image of the substrate using a detector, camera, or a photometer. Optionally, the system can be configured to utilize lighting sources to help obtain the image of the substrate. At block 412, the system can be configured to determine the cell count or the cell density on or within the substrate. At decision block 414, the system determines if the cell count or cell density exceeds a certain threshold level. If the detected cell count or cell density exceeds the threshold level, the system at block 416 generates a notification comprising a probability that the substrate is ready for implantation. Alternatively, the system can be configured to tag or identify the substrate as ready for implantation at block 416. At block 418, the system can be configured to output the notification and end the process at block 420.

If the system determines that the cell count or cell density does not exceed a certain threshold level, the system can be configured to compare the detected cell count or the detected cell density to other threshold levels stored within the threshold levels database to determine at block 422 a specific period of time that the substrate is likely to be ready for implantation. In an embodiment, the threshold levels database comprises a plurality of thresholds associated with specific periods of time typically necessary to grow cells on or within a substrate based on the current detected cell count or cell density. The specified periods associated with the plurality of threshold levels are determined based on historical analysis of typical cell growth within or on a particular substrate. In determining a specific period of time when the substrate is likely to be ready for implantation, the system can take into account the current number of days the cells on or within the substrate have been allowed to grow.

At block 420, the system allows the cells to continue to grow within or on the substrate for the specific period of time determined at block 422. In any embodiment, the system can be configured to repeat the process by positioning the substrate under or within the system or microscope at block 404.

Figure 4B:
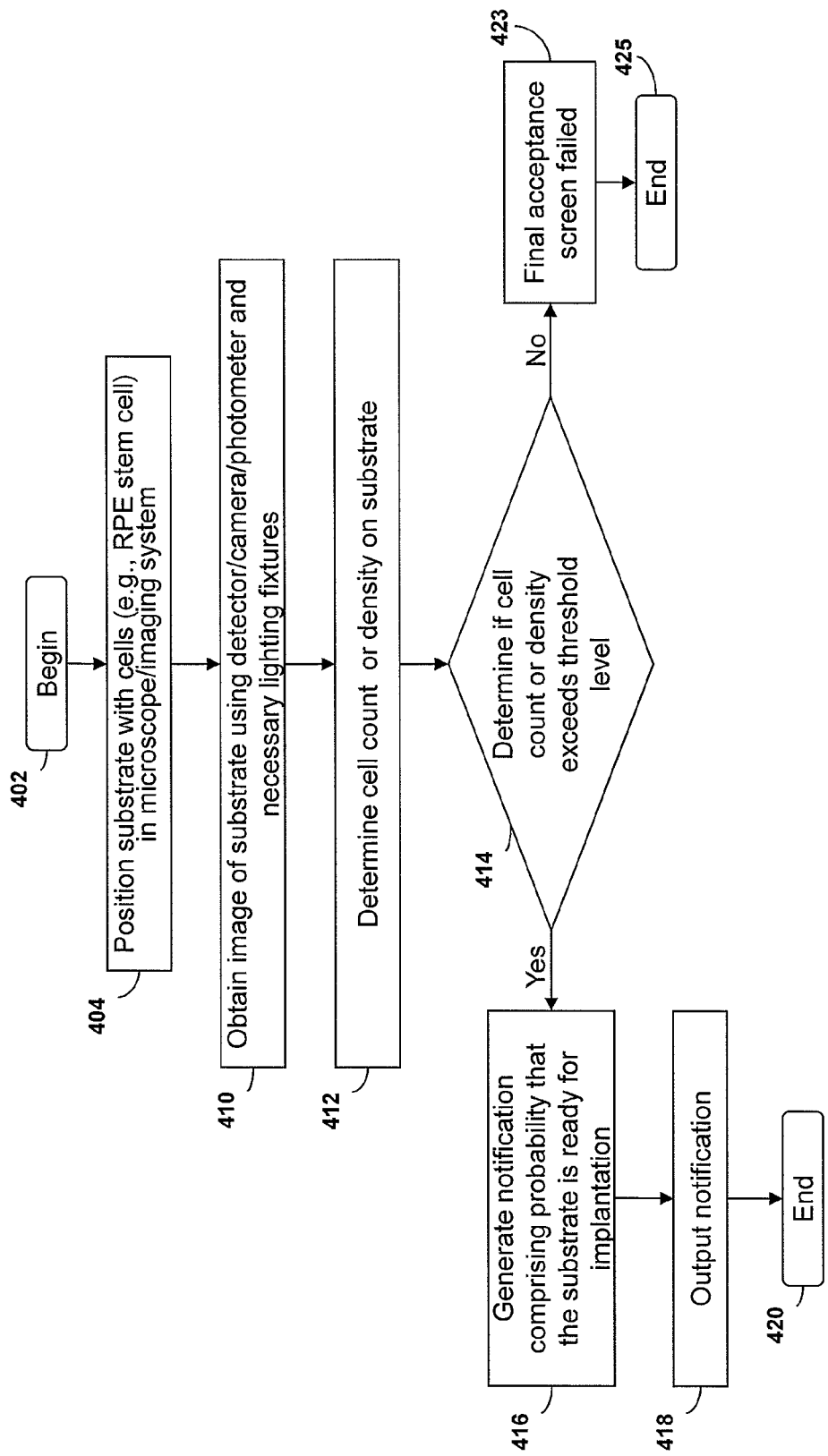
FIG. 4B is a flow chart depicting an embodiment of an in vitro substrate verification testing based on cell count without a feedback loop.

FIG. 4B is a flow chart illustrating a process similar to the process illustrated in FIG. 4 except the process illustrated in FIG. 4B does not allow for the cells to continue to grow on or within the substrate if the substrate fails the cell count or cell density threshold level test. In an embodiment, the system can be configured at block 414 to determine if the cell count or cell density exceeds the threshold level. If the cell count or cell density exceeds the threshold level, the system at block 416 generates a notification or tags the substrate as likely ready for implantation or provides a probability that the substrate is ready for implantation. The system at block 418 can be configured to output the notification and end the process at block 420.

If the system determines that the cell count or cell density does not exceed a specified threshold level, then the system can identify or tag the substrate as having failed the final acceptance screen at block 423 and end the process at block 425.

Figure 5:
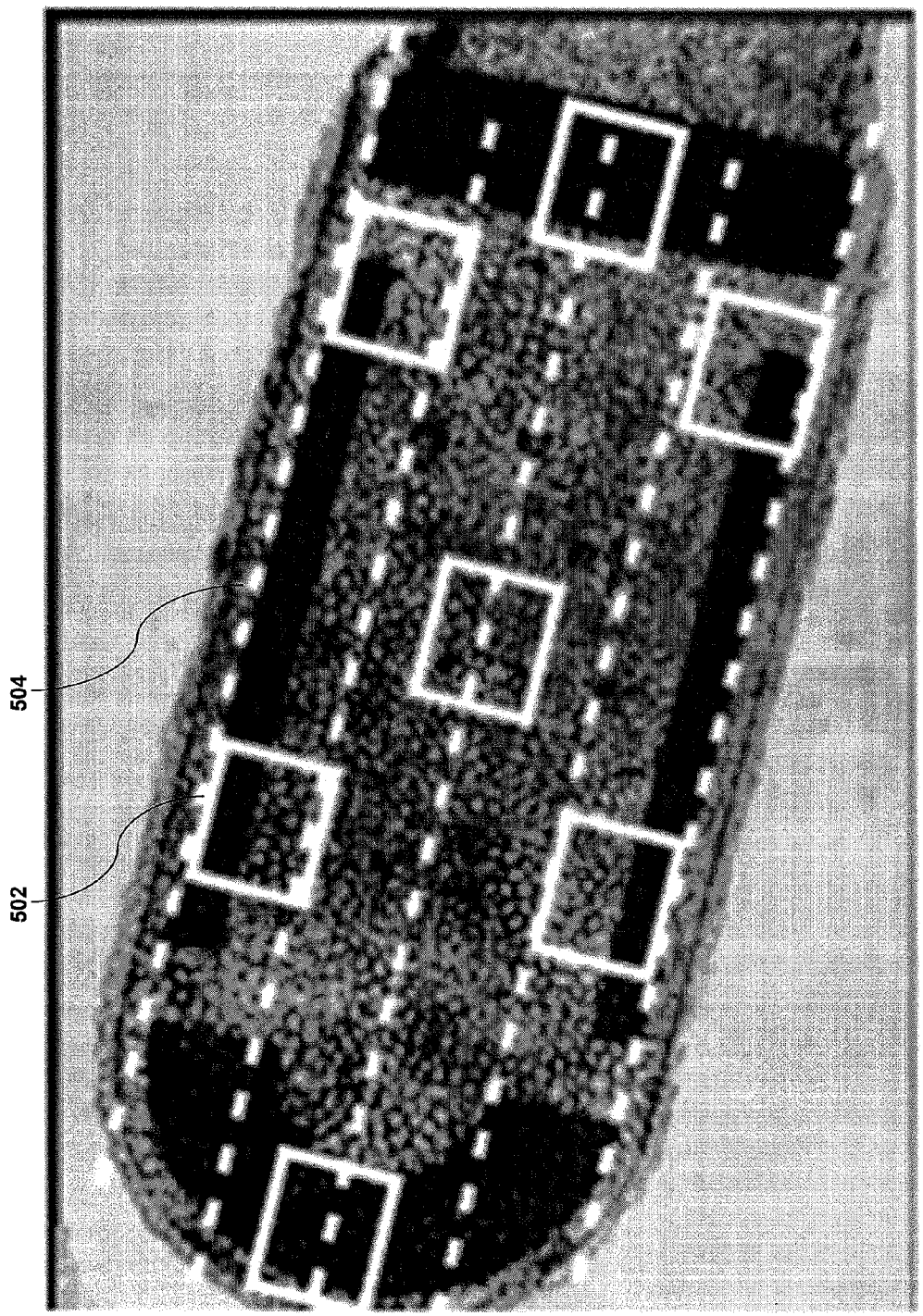
FIG. 5 is a schematic diagram of an embodiment of a substrate comprising cells.

FIG. 5 is a schematic drawing illustrating a substrate comprising cells growing on or within the substrate. In an embodiment, the image of the substrate can be augmented to include markings 502, 504, for example squares, rectangles 502, and lines 504. The augmented image of the substrate can be presented to a user. A user can utilize the augmented image of the substrate to count the number of cells within the square or rectangular or lined off regions. Based on counting the cells within these defined areas, the user can extrapolate the number of cells growing on or within the substrate based on the number of cells counted within a particular lined off region. The user can then input the determined number of cells into the system wherein the system can be configured to prepare the cell count or cell density to threshold levels to determine whether the substrate is ready for implantation in accordance with the various processes described above. Alternatively, the system can be configured to use image processing techniques and/or other devices to count the number of cells automatically without user intervention.

Figure 6:
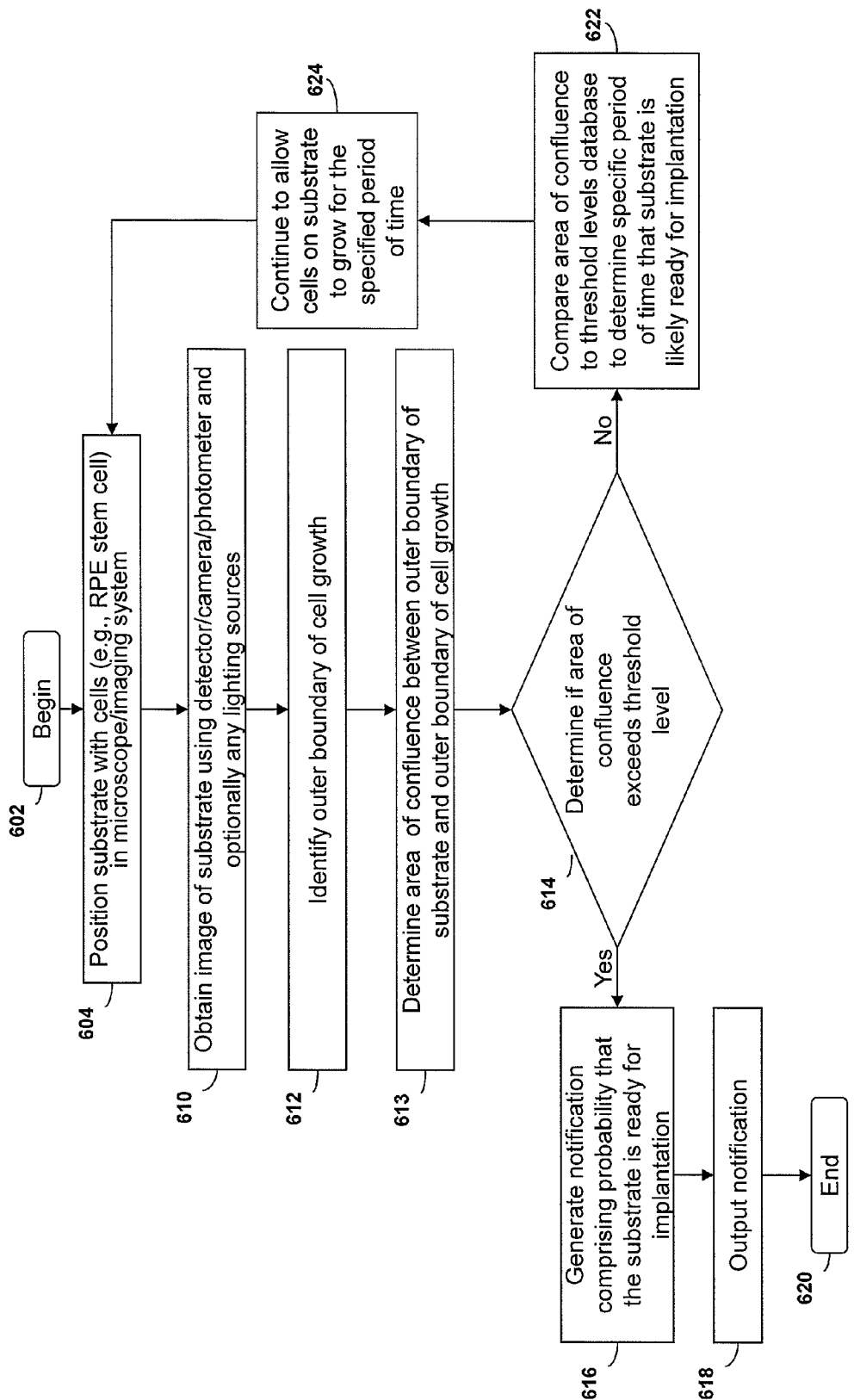
FIG. 6 is a flow chart depicting an embodiment of an in vitro substrate verification testing based on confluence testing.

FIG. 6 is a flow chart of a process for using degree of confluence, for example 100% confluence, to determine whether a substrate is ready for implantation. The process can begin at block 602 wherein the substrate is positioned within or under a microscope or other imaging system at block 604. At block 610, the system can be configured to obtain an image of the substrate using a camera and optionally using any light sources. At block 612, the system can be configured to analyze the obtained image to identify the outer boundary of cell growth on the substrate. At block 613, the system can be configured to determine the area of confluence between the outer boundary of the substrate and the outer boundary of cell growth. Alternatively, the system can be configured to determine the distance between the outer boundary of the substrate and the outer boundary of the cell growth. In an embodiment, the dimensions of the substrate are standardized, therefore, the system can be configured to determine or know the outer boundary of the substrate. At decision block 614, the system can be configured to determine if the area of confluence exceeds a threshold level. If the system determines that the area of confluence exceeds the threshold level, the system at block 616 can be configured to generate a notification comprising a probability that the substrate is ready for implantation. At block 618, the system can be configured to output the notification and end the process at block 620. If the system determines that the area of confluence does not exceed a threshold level, the system at block 622 can be configured to compare the detected are of confluence to other threshold levels stored within threshold levels database to determine a specific period of time that the substrate will be likely ready for implantation. At block 624, the system allows the cells to continue to grow on the substrate for the specified period determined at block 622. In an embodiment, the system can be configured to repeat the process by positioning at block 604 the substrate under a microscope or other imaging system after the specified period has ended.

Figure 6B:
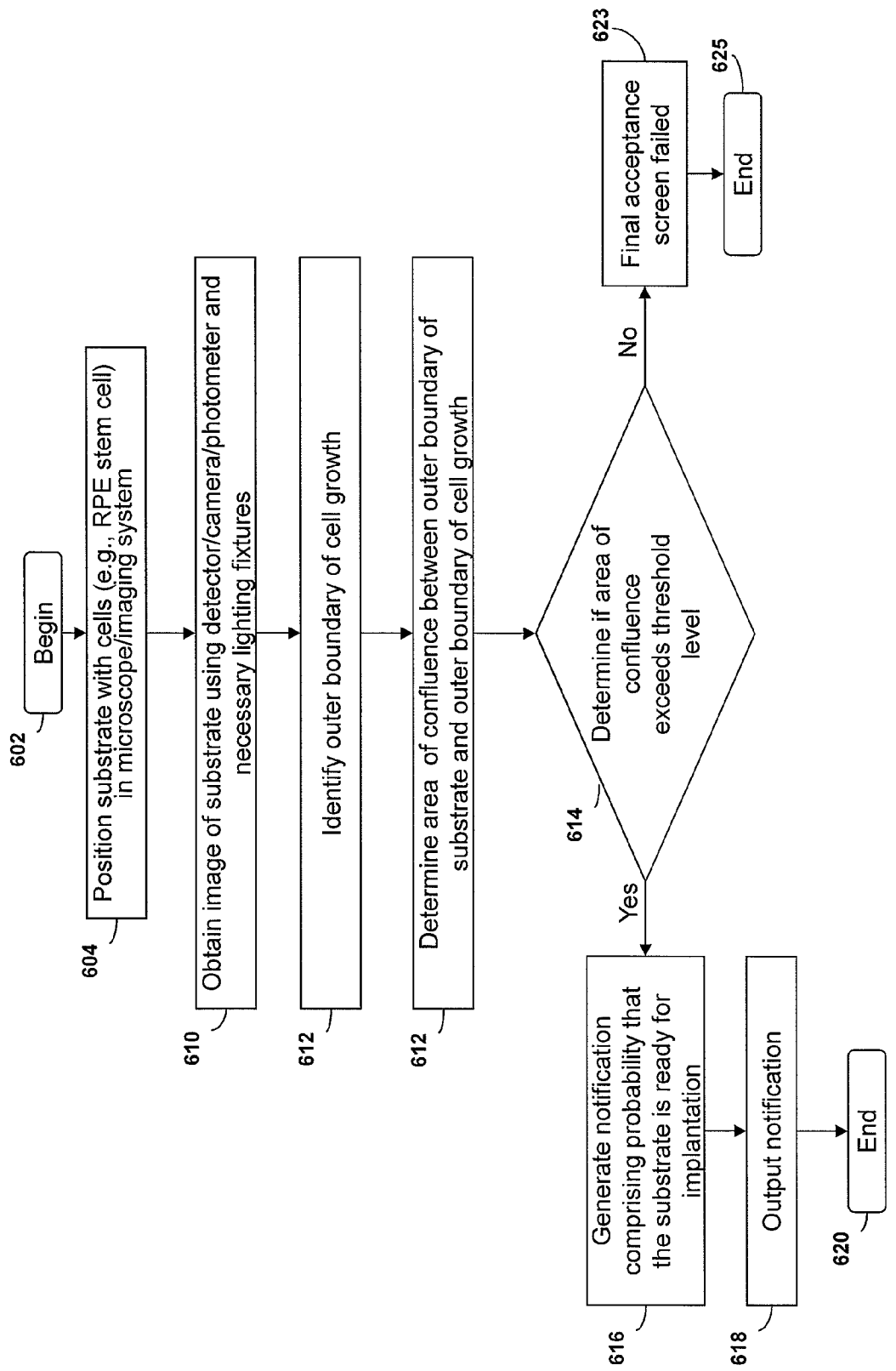
FIG. 6B is a flow chart depicting an embodiment of an in vitro substrate verification testing based on confluence analysis without having a feedback loop.

FIG. 6B is a flow chart illustrating a process similar to the process illustrated in FIG. 6 except the system does not allow the cells to continue to grow on or within the substrate if the substrate fails to pass the confluence test. At block 614, the system determines if the detected area of confluence exceeds the threshold level. If the detected area does exceed the threshold level, the system at block 616 can be configured to generate notification comprising a probability that the substrate is ready for implantation. At block 618, the system outputs notification and ends the process at block 620. If the system determines that the detected area of confluence does not exceed a threshold level, the system at block 623 indicates or tags the substrate or generates a notification that the substrate failed the final acceptance screen at which point the process ends at block 625. In an embodiment, if the substrate fails the final acceptance screen, the substrate can be destroyed and/or discarded.

Figure 7:
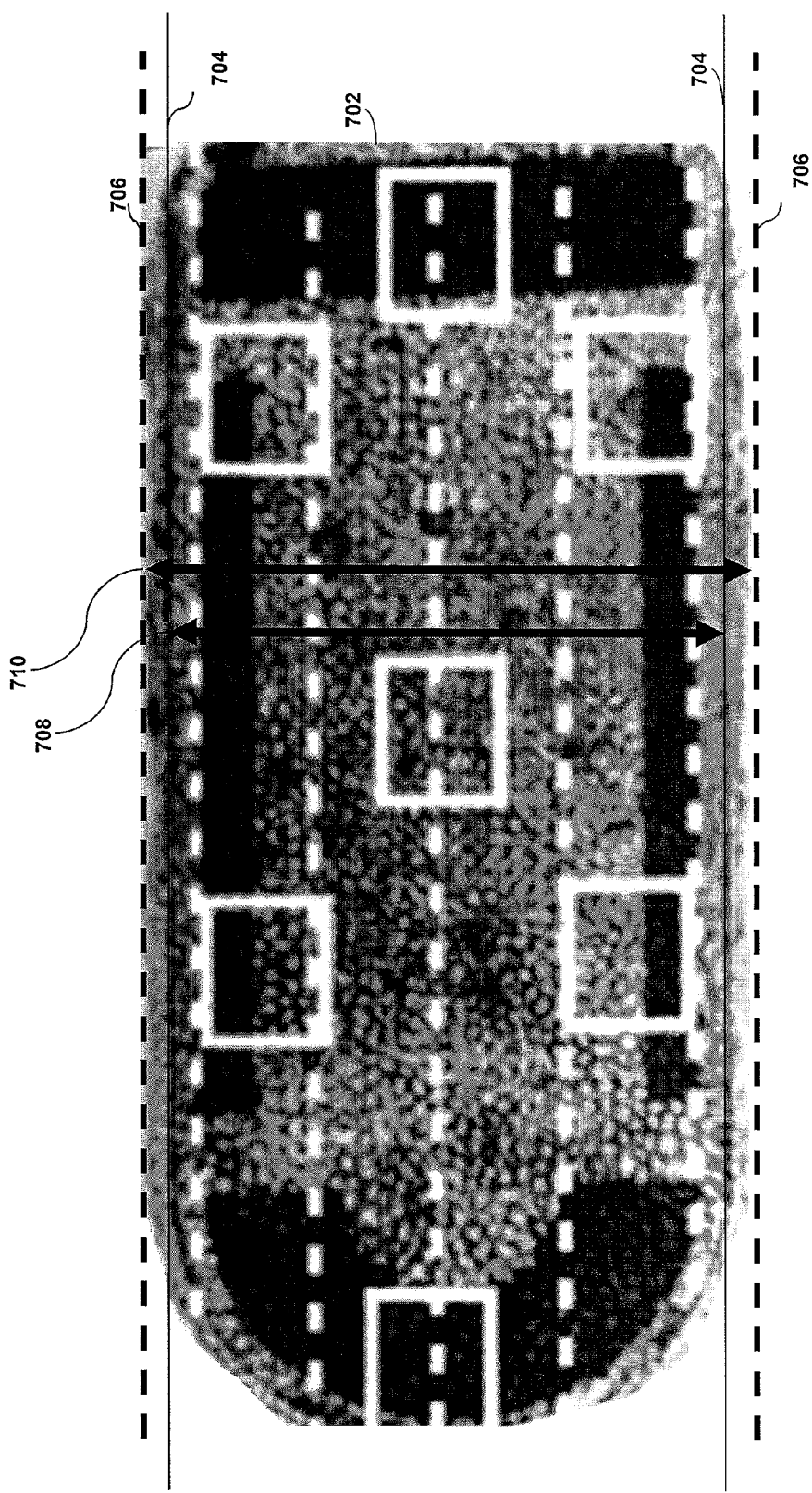
FIG. 7 is a schematic diagram illustrating an embodiment of a substrate comprising cells.

FIG. 7 is a schematic diagram illustrating a process for determining the area of confluence or a distance between the outer boundary of the substrate and the outer boundary of cell growth. The substrate 702 can comprise an outer boundary 704. As the cells in or on the substrate 702 grow, the cell count or cell density can reach a certain point where the cells start to grow beyond the substrate boundary as indicated by the dotted lines 706. By measuring the area or distance between the outer boundary of the substrate and the outer boundary of the cell growth, the system can be configured to utilize this measurement to determine whether a substrate is likely ready for implantation.

Figure 8:
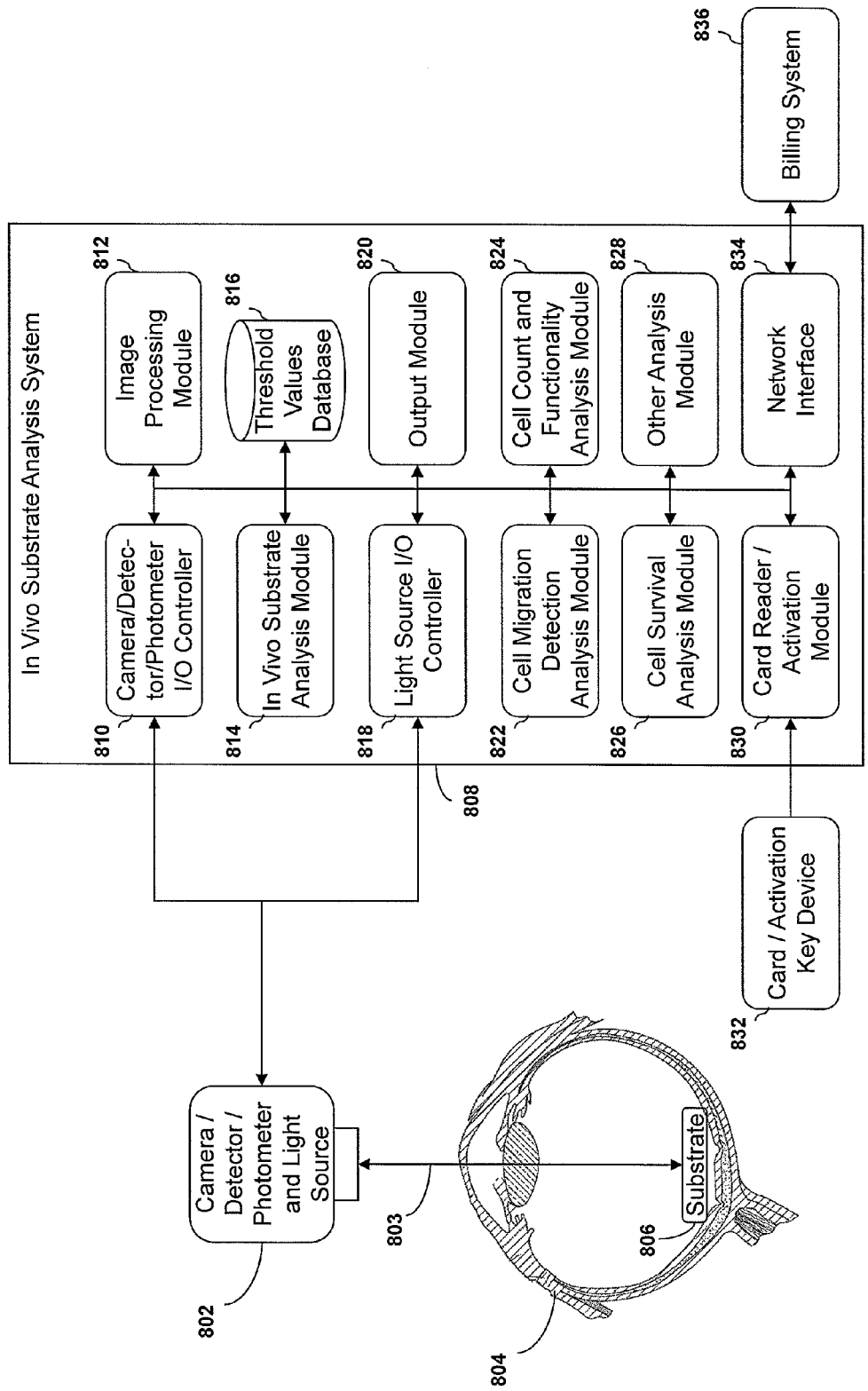
FIG. 8 is a block diagram depicting a high level overview of an embodiment of an in vivo substrate analysis system.

FIG. 8 is a block diagram illustrating an embodiment of an in vivo substrate analysis system configured to analyze an implanted substrate 806 that is positioned within an eye 804. As discussed above, the system can be used to determine whether cells on and/or within a substrate, or whether the substrate, are performing acceptably in the body or whether further analysis or surgical action is required.

In an embodiment, the in vivo substrate analysis system comprises a camera, detector, or photometer 802. The camera 802 can also comprise a light source. The camera can be configured to shine light 803 into the eye 804 and onto the substrate 806. The camera 802 can be configured to capture the reflected light off the substrate to generate an image of the substrate. Alternatively, the camera can be configured to filter out the light directed into the eye and can be configured to detect the autofluorescence generated by the cells within or on the substrate.

The data captured by the camera 802 can be inputted into camera input-output controller 810. The data from the camera 802 can be processed using image processing module 812. The data can also be analyzed using in vivo substrate analysis module 814. The in vivo substrate analysis module can be configured to interact with other modules within the in vivo substrate analysis system. For example, the in vivo substrate analysis system can interact with cell migration detection analysis module 822 to determine if cells have migrated off the substrate 806 and into other areas of the eye 804. Additionally, the in vivo substrate analysis module 814 can interact with cell count and cell functionality analysis module 624 to determine the number of cells on or within substrate 806 and how those cells are functioning. The in vivo substrate analysis module 814 can also interact with cell survival analysis module 826. The in vivo substrate analysis module 814 can also interact with other analysis modules 828.

In an embodiment, the in vivo substrate analysis system is a stand alone system positioned within an operating room or doctor's office. The system can be utilized by a doctor or other user to analyze a substrate implanted within a user's eye. In an embodiment, the in vivo substrate analysis system can be activated when the user uses a card or other activation key device to activate the in vivo substrate analysis system. For example, for each use of the in vivo substrate analysis system, the user can insert an activation card into a card reader module 830. The system can be configured to authenticate the card and allow the user to utilize the in vivo substrate analysis system upon activation. In an embodiment, the activation card acts as a billing system because the user and/or patient must purchase a new card in order to activate the in vivo substrate analysis system. Alternatively, the in vivo substrate analysis system utilizes network interface 834 to communicate with billing system 836 to bill or generate an invoice each time the in vivo substrate analysis system is utilized.

Figure 9:
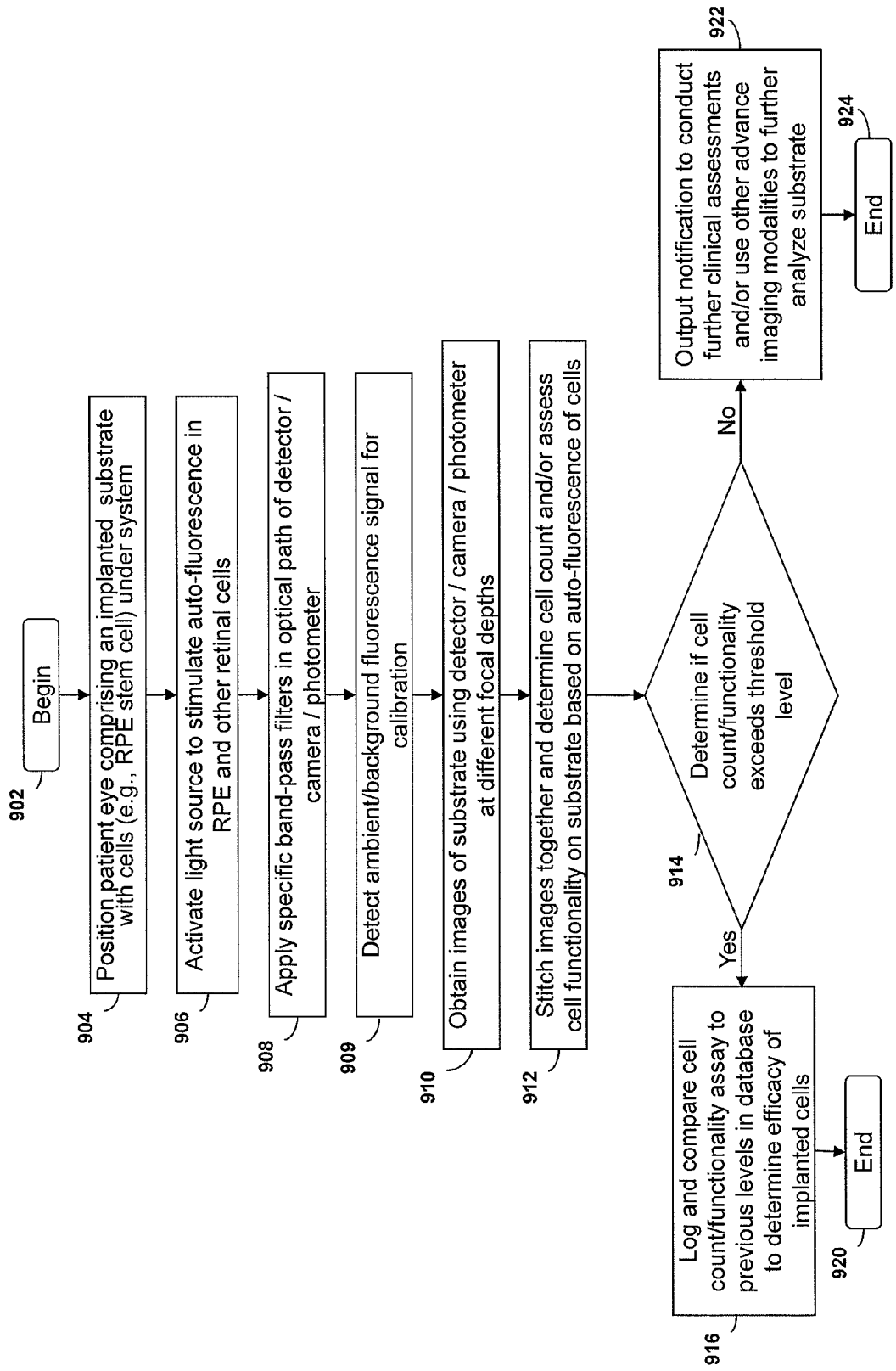
FIG. 9 is a flow chart depicting an embodiment of a process for analyzing an implanted substrate.

FIG. 9 is a flow chart illustrating a process for determining cell count and/or cell functionality of an implanted substrate. The process can begin at block 902 by positioning under the system a patient eye comprising an implanted substrate having cells, for example, RPE stem cells. At block 906, the system can be configured to activate a light source to stimulate autofluorescence in the cells, for example RPE cells or other retinal cells. At block 908, the system can be configured to apply specific band pass filters to the optical path of the detector, thereby filtering out any light generated by the light source and/or only allowing light generated by the autofluorescence of the RPE cells and other retinal cells. At block 909, the system can be configured to detect ambient and/or background fluorescent signals to calibrate the system in order to filter out such ambient and/or background fluorescent signals. At block 910, the system can be configured to obtain an image of the substrate using the detector at different focal depths. In an embodiment the system utilizes a SLO (scanning laser ophthalmoscope) imaging system to visualize the details of the substrate and other tissues within the eye. In general, SLO imaging allows for images of the eye to be taken in an x-y direction at various z depths. Accordingly, in order to obtain as three-dimensional image of the eye, the system can be configured to obtain multiple x-y images of the eye at different focal depths along the z axis. At block 912, the system can be configured to stitch together or combine the plurality of images taken using the SLO imaging system. The system can then use the generated three-dimensional image to determine cell count and/or assess cell functionality on the substrate based on the autofluorescence of the cells. At block 914, the system determines if the cell count and/or functionality exceeds the threshold level. If the system determines that the cell count and/or functionality does exceed the threshold level, the system at block 916 logs and/or compares the cell count functional assay to previous levels stored in a database to determine the efficacy of the implanted cells. If at block 914 the systems determines that the cell count and/or functionality is below a threshold level, then the system can be configured output a notification to a user to conduct further clinical assessments and/or use other advanced imaging modalities to further analyze the substrate at block 922.

Figure 10:
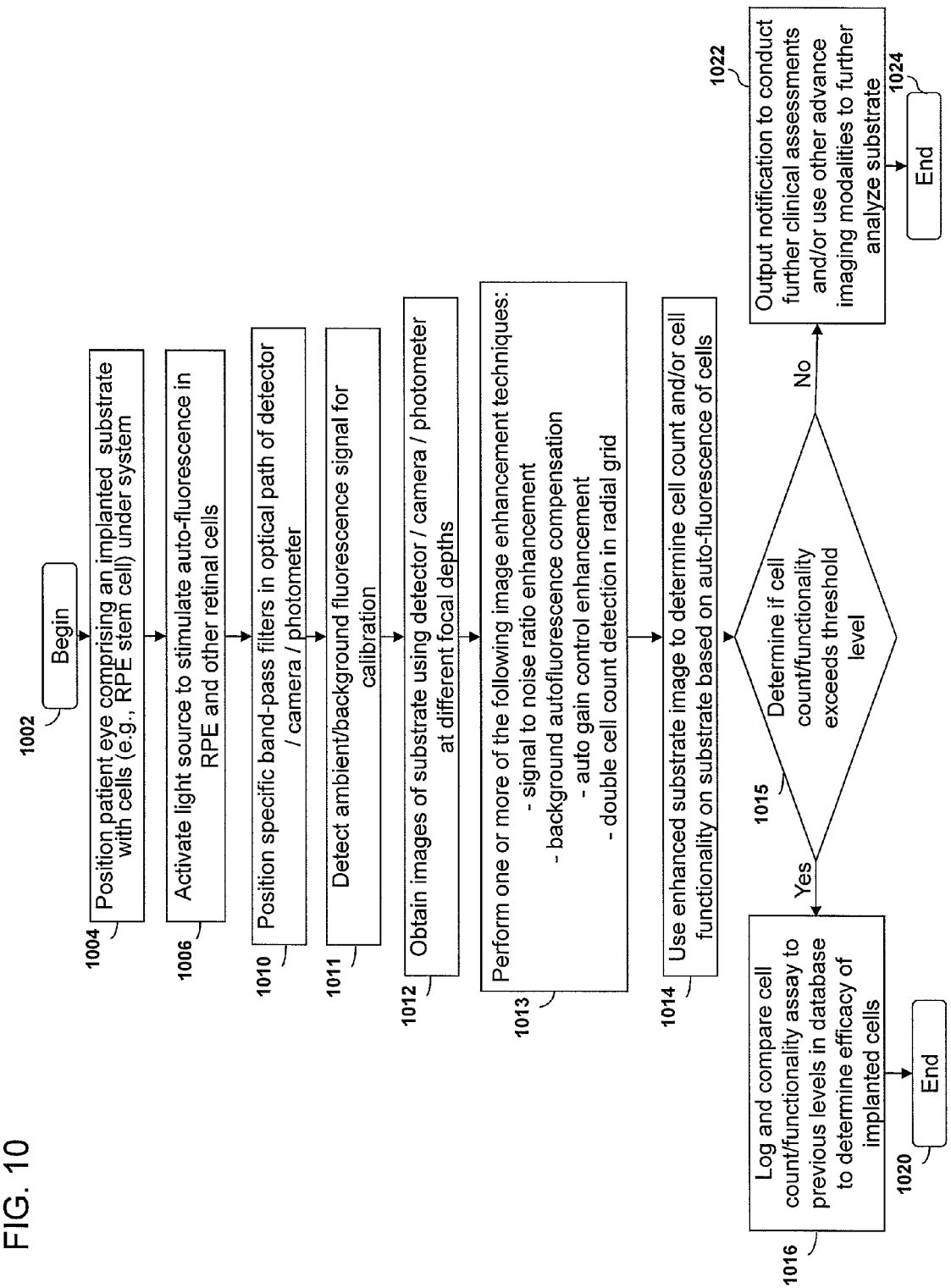
FIG. 10 is a flow chart depicting an embodiment of a process for analyzing an implanted substrate using image enhancement techniques.

FIG. 10 is a flow chart of a process similar to the process illustrated in FIG. 9 except that the obtained image of the substrate using the camera undergoes additional imaging enhancement techniques to produce a more clear image. For example, at block 1013, the system can be configured to perform one or more of the following image enhancement techniques on the obtained image of the substrate:

Signal to noise ratio enhancement

Background autofluorescence compensation

Auto gain control enhancement

Double cell count detection in radial grid

Figure 11:
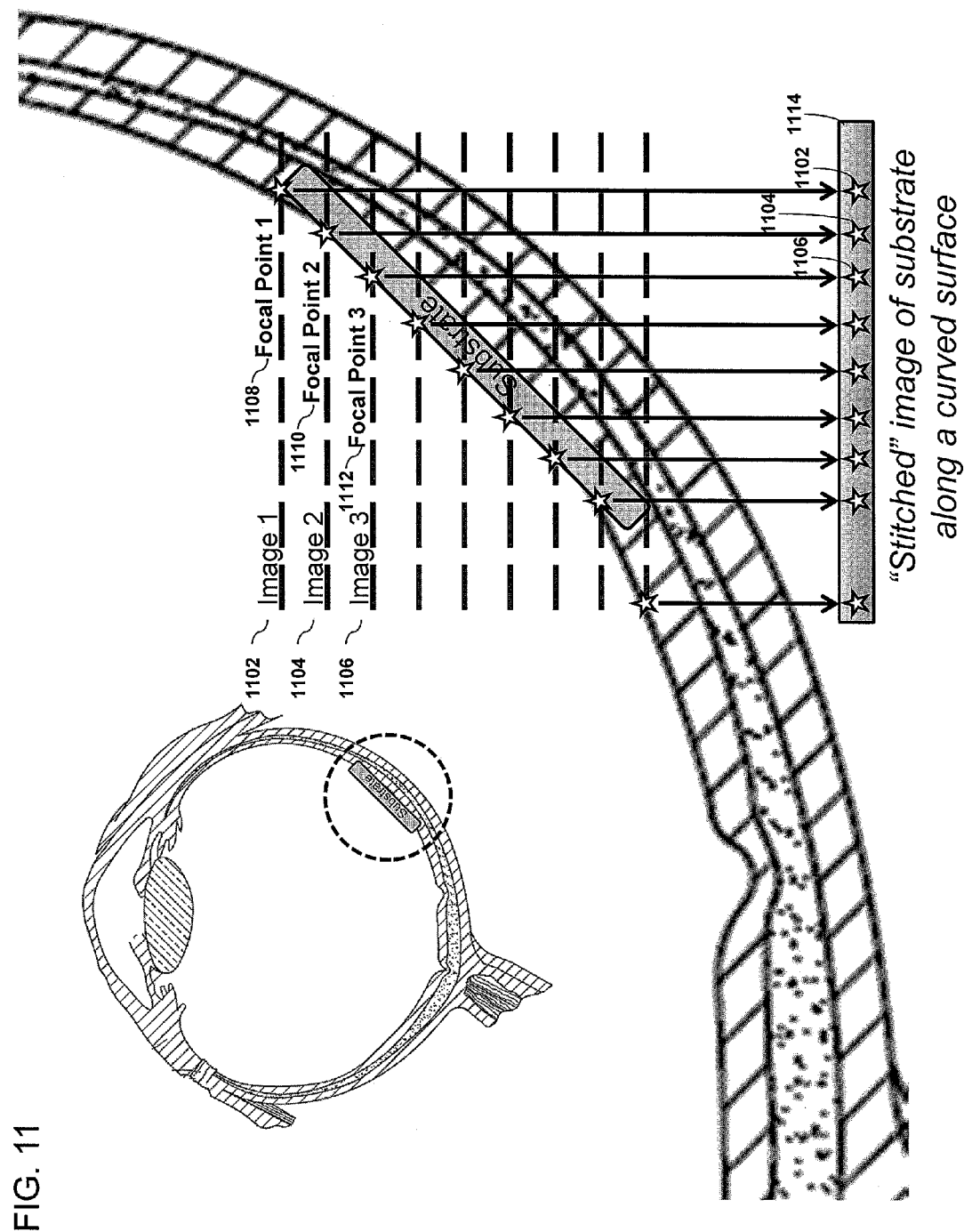
FIG. 11 is a schematic diagram illustrating in vivo imaging of a substrate using confocal SLO image stitching technique.

FIG. 11 is a schematic drawing illustrating how a plurality of two dimensional images on the x-y plane is taken or scanned using a SLO imaging system or other camera or detective device at various z depths or z positions. In the illustrated schematic, Image 1 1102, which is a two-dimensional image in the x-y plane, is taken at a depth of z1 or at Focal Point 1 1108. Another two-dimensional image in the x-y plane, Image 2 1104, is taken at a depth of z2 or Focal Point 2 1110. Similarly, a plurality of two-dimensional images in the x-y plane is taken at a plurality of z depths along the implanted substrate. The resulting plurality of two dimensional images in the x-y plane 1102, 1104, 1106 taken from varying z depths are then combined or "stitched" together to generate a fully formed image of the substrate 1114 as discussed below.

In an embodiment, the system determines where to start and end scanning, either automatically or after receiving input from a user. In other words, the system determines the maximum and minimum focal depths. The system can scan sequentially between the maximum and minimum focal depths in increments to collect a plurality of two dimensional images in the x-y plane. In some embodiments, the system automatically determines the maximum and minimum focal depths by detecting regions encompassed by boundary markers that are placed on the substrate. Boundary markers are discussed in more detail below. The system can scan the region within the boundary markers. The system can also receive input from a user to set the maximum and minimum focal depths.

In an embodiment, the system is not changing magnification during the scan, but is only adjusting focus along the z axis. The increments in focal depth that the system scans can range from about 0.01 µm to about 20 µm. For example, the system can be configured to scan or take two dimensional images in the x-y plane of the substrate at about every 1 µm, about 2 µm, about 3 µm, about 4 µm, about 5 µm, about 6 µm, about 7 µm, about 8 µm, about 9 µm, about 10 µm, about 11 µm, about 12 µm, about 13 µm, about 14 µm, and about 15 µm. In some embodiments, the increments in scanning can be adjusted at the start of scanning of an eye. In other embodiments, the increments in scanning can be adjusted dynamically during scanning of an eye. For example, if the substrate is positioned at an angle, the increment can be adjusted to be smaller than when the substrate is nearly flat. To do so, the system determines the pitch of the substrate from the maximum and minimum focal depths. The system can automatically or manually determine an appropriate focal depth interval or increment depending on the pitch of the substrate.

After the system completes scanning or taking a plurality of two dimensional images in the x-y plane at varying z depths or z positions, those images can be combined in a number of different ways. In an embodiment, the stack or plurality of two dimensional images in the x-y plane can be combined to form a three-dimensional map or image of the substrate, surrounding area of the eye, and neighboring tissue. The system can use the three-dimensional map to identify and/or count cells therein, for example stem cell-derived RPE cells, and identify xyz coordinates of the cells. In some embodiments, the system identifies and/or counts fluorescence or other light emitted from fluorophores and/or other tags coupled to the cells from the three-dimensional map. The system can also identify the xyz coordinates of the fluorophores and/or other tags coupled to the cells from the three-dimensional map.

Alternatively, the stack or plurality of two dimensional images in the x-y plane can be made transparent to a certain degree and be superimposed and/or merged to generate a single two dimensional image. The system can use the single two-dimensional image to identify and count cells therein, for example stem cell-derived RPE cells, and identify xyz coordinates of the cells. The system can identify the z coordinate based on at which z depth the two dimensional x-y plane image containing the cell was taken. In some embodiments, the system identifies and/or counts fluorescence or other light emitted from fluorophores and/or other tags coupled to the cells from the single two-dimensional image. The system can also identify the xyz coordinates of the fluorophores and/or other tags coupled to the cells from the single two-dimensional image.

In another embodiment, the stack or plurality of two dimensional images in the x-y plane can be mapped onto a new two-dimensional image with or without the z depth data incorporated therein according to an algorithm. In such an embodiment, each two-dimensional image in the x-y plane can be analyzed by the computer system to determine whether the image includes any cells or fluorescence or other light emitted from a fluorophore or other tag coupled to cells that are in focus. If so, the computer system can determine the x-y location of the in-focused objects and identify the xyz coordinates of the in-focused objects. The computer system can also store and transpose or map the identified xy coordinates of objects in-focus on a new two-dimensional image. The z coordinates of the objects in-focus can simultaneously be stored in the computer system, although not displayed on the two-dimensional image. The computer system can repeat this process for all collected two-dimensional images in the x-y plane and place in-focus imaged objects on the new two-dimensional image. All respective z-depth data of the objects can be stored in the computer system.

The computer system can further use the new two-dimensional image to identify and count cells therein, for example stem cell-derived RPE cells, and identify xyz coordinates of the cells. The system can identify the z coordinate based on at which z depth the two dimensional x-y plane image containing the cell was taken. In some embodiments, the system identifies and/or counts fluorescence or other light emitted from fluorophores and/or other tags coupled to the cells from the new two-dimensional image. The system can also identify the xyz coordinates of the fluorophores and/or other tags coupled to the cells from the new two-dimensional image.

Figure 11B:
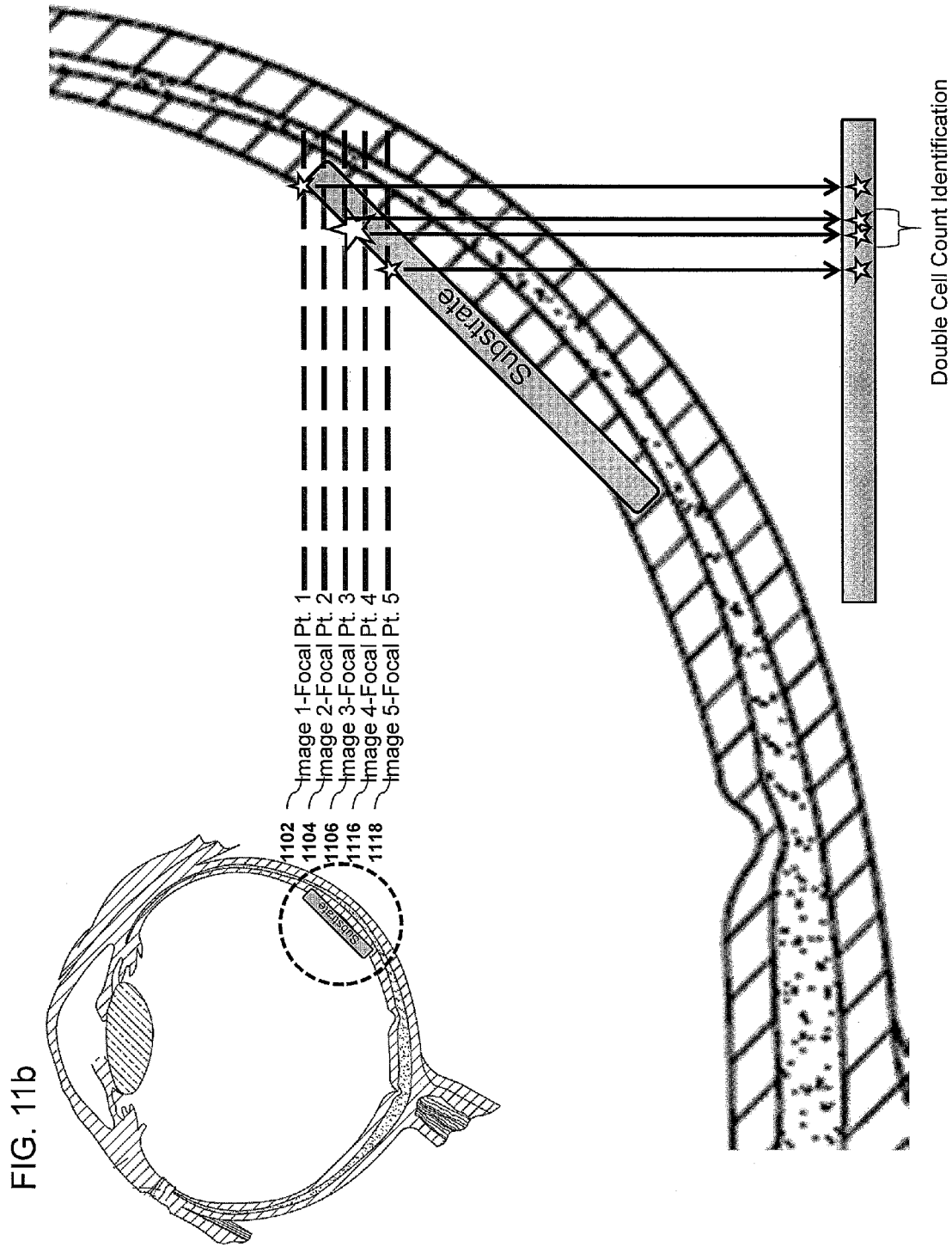
FIG. 11B is a schematic diagram of a method for determining double cell counting in a radial grid.

FIG. 11B is a schematic drawing illustrating a process or method for identifying double counting of a single cell in a radial grid. In the illustrated schematic, a single large cell appears in two-dimensional images in the x-y plane taken from both focal points 3 and 4. Without an algorithm for preventing double counting of a single cell, the system will count these as two cells when there is actually only one cell.

In an embodiment, the computer system is configured to detect a cell in the same x-y position that appears in two or more two-dimensional images in the x-y plane taken from neighboring z-depths or positions. The computer system then determines whether these two dimensional images in the x-y plane are referring to an identical cell or two or more separate cells that are located very close to each other. To do so, the computer system can compare the size of the detected object to pre-stored data of normal cell sizes for a particular cell(s). If the size of the detected object is much larger than the normal cell size, then the computer system can determine that it has detected two or more separate cells rather than a single cell.

Alternatively, the system can further analyze additional two dimensional images in the x-y plane taken from z-depths adjacent or near those at issue to determine a change in fluorescence or light emitted by a fluorophore(s) or other tag coupled to the detected object over that region of z-depths. The computer system can compare the change in fluorescence or light emitted, for example a bell curve in intensity across varying z-depths, to pre-stored data of emitted fluorescence or light curves for a single cell and two or more cells to determine whether it has detected a single cell or two or more cells. For example, if a fluorescence intensity curve is monotonic on both sides of the peak of the curve, then the computer system has detected a single cell. If the fluorescence intensity curve is non-monotonic on either side of the peak of the curve, then the computer system has detected two or more cells. If the computer system determines that it has detected a single cell that appears in more than one two-dimensional image in the x-y plane, then the computer system can subtract the additional counts to adjust the cell count.

In an embodiment, photoacoustic imaging can be used to image implanted cells in vivo, for example stem cell-derived RPE cells. For example, non-ionizing laser pulses can be directed at the tissue area where implanted cells are located. The tissue and implanted cells within the tissue absorb some of such directed energy and convert it to heat, resulting in ultrasonic emission. Ultrasonic detectors or transducers can be used to detect such ultrasonic waves to form images. Because optical absorption is closely related to physiological properties, certain algorithms can be used to generate two-dimensional or three-dimensional images using the detected ultrasonic waves. In some embodiments, optical coherence tomography imaging (OCT) can be used in connection with ultrasound systems and energy to view cells or detect the presence of cells, for example stem cell-derived RPE cells or any other type of cell. In some embodiments, photoacoustic imaging can be employed to determine the density of cells in vivo, for example the density of stem cell-derived RPE cells on a substrate that is implanted in an eye. In certain embodiments, catheter-based OCT and ultrasound systems can be employed for targeted areas deep in the body, for example in the knee or any other area.

In an embodiment, a reflectometer can be used to indirectly obtain structural information of photoreceptors within an eye in vivo where stem cell-derived RPE cells are implanted. A reflectometer is a device for determining the physiological health of a photoreceptor cell(s) in an eye. Use of a reflectometer can be an alternative method of testing functionality of implanted stem cell-derived RPE cells. By using a reflectometer in some embodiments it may not be not be necessary to take a plurality of two dimensional x-y images along a z-axis to count the number of cells. Although a reflectometer does not measure the stem cell-derived RPE cells directly, it measures the health of rhodopsin pigments in the photoreceptors, thereby assessing the state of photoreceptors in the eye. Reflectometers can be used to determine the change in reflected light based on the state of photoreceptors in an eye. When light is directed at an eye, photons hit photoreceptors and molecules therein changing the configuration from cis to trans. In some embodiments, the wavelength of such light can be from about 300 nm to about 800 nm and preferably between 400 nm and 700 nm. The molecules require some time to switch back to their original configuration to function properly. A reflectometer can detect and plot this relaxation, recovery, or adaptation time constant that is required for a photoreceptor to be functional again. Since normal or average relaxation time constants are well known, the detected relaxation time of the cells can be compared to pre-stored average time constants to determine the functionality of the photoreceptors, which in turn is an indication of functionality of implanted stem cell-derived RPE cells.

Adaptive optics with or without a scanning laser ophthalmoscope can also generally be used to monitor photoreceptors to determine the state of photoreceptors in an eye in vivo where stem cell-derived RPE cells are implanted. Systems and devices for adaptive optics can measure distortions in light in biological tissues and correct such distortions. In some embodiments, backscattered light from the targeted area can be used.

Figure 12:
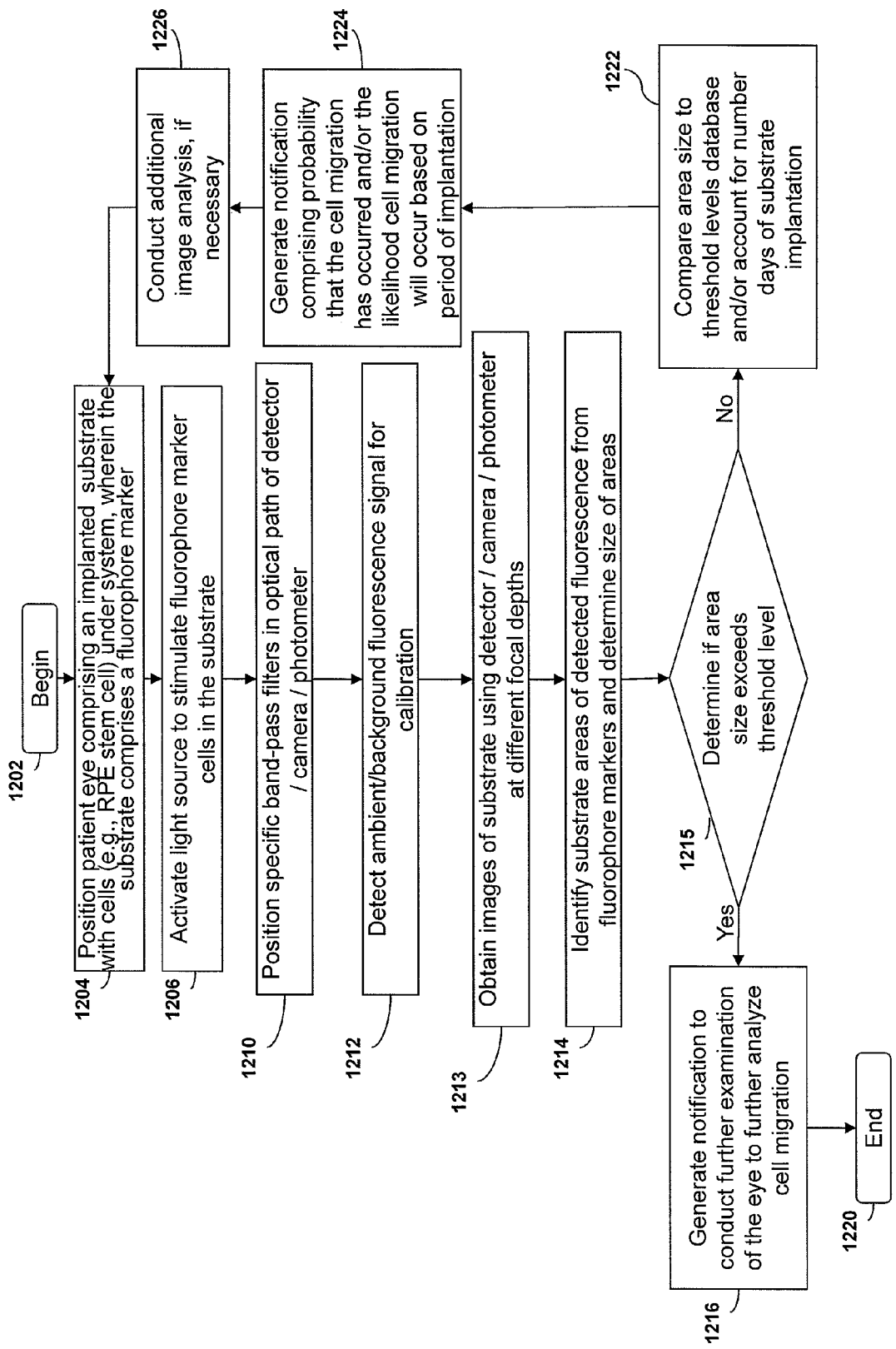
FIG. 12 is a flow chart depicting an embodiment of a process for analyzing an implanted substrate comprising fluorophore markers.

FIG. 12 is a flow chart illustrating a process for identifying cell migration off a substrate. The process can begin at block 1202 by positioning under the system a patient eye comprising an implanted substrate having cells, wherein the substrate comprises a fluorophore marker. At block 1206, the system can be configured to activate a light source to simulate the fluorophore marker cells in the substrate. At block 1210, the system can be configured to position specific band pass filters in the optical path of the detector to block out light generated from the light source. At block 1212, the system can be configured to detect ambient or background fluorescent signal in order to calibrate the system. At block 1213, the system can be configured to obtain images of the substrate using a camera at different focal depths. As described above, an SLO imaging system can be utilized for obtaining the images. At block 1214, the system can be configured to identify areas of the substrate where fluorescence from the fluorophore markers can be detected. The system can also be configured to determine the size of the detected areas. At decision block 1215, the system can be configured to determine if the detected areas exceed a threshold level. If the system determines that the detected area does exceed a threshold level, the system can be configured at block 1216 to generate a notification to conduct further examination of the eye to further analyze cell migration at which point the process can end at block 1220. If the system determines that the area does not exceed a threshold level, the system can be configured to compare the threshold area to threshold levels stored in a threshold levels database and/or account for the number of days the substrate has been implanted in the eye at block 1222. At block 1224, the system can be configured to generate a notification comprising the probability that cell migration has occurred and/or the likelihood cell migration will occur based on the period of implantation. At block 1226 the system can be configured to perform additional imaging analysis if necessary and/or the system can be configured to repeat the process by returning to block 1204.

Figure 13B:
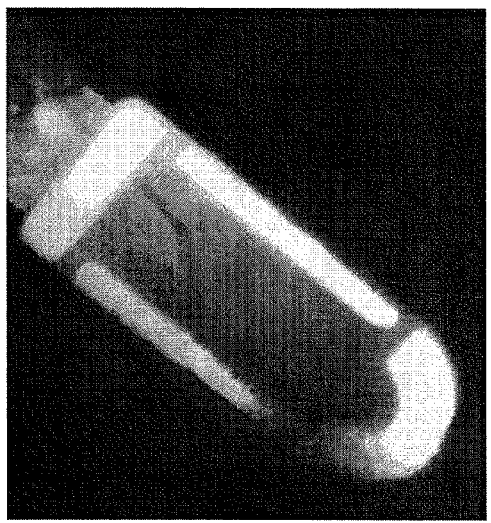
FIG. 13B illustrates an implanted substrate comprising boundary markers.
Figure 13A:
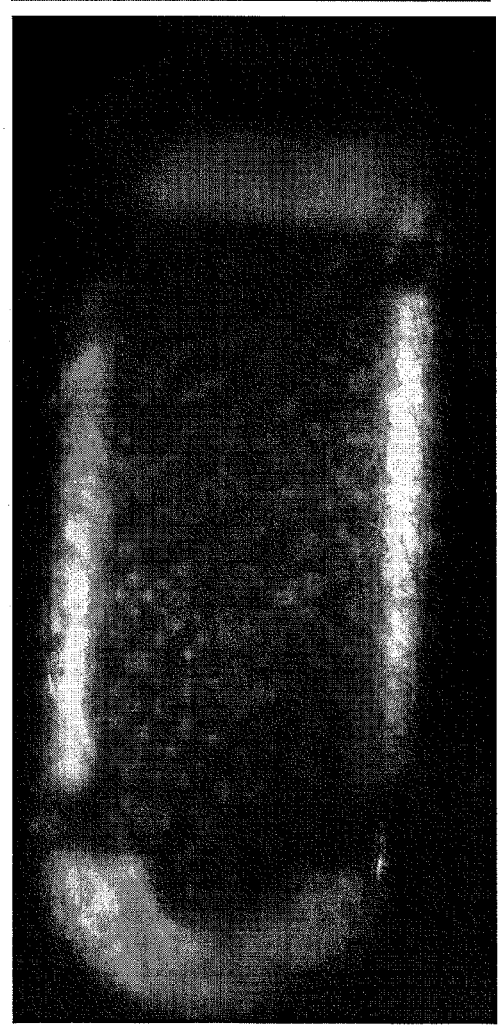
FIG. 13A illustrates an implanted substrate comprising cells with stimulated autofluorescence.

Generally, FIG. 13A illustrates a substrate comprising cells with stimulated autofluorescence and FIG. 13B illustrates a substrate without cells comprising boundary markers. More specifically, FIG. 13A illustrates embodiments of in vitro, non-confocal FAF images of hESC-RPE seeded substrates and FIG. 13b illustrates unseeded substrates. Compared to the unseeded substrate, the seeded substrate shows the hexagonal lattice structure of the hESC-RPE cells located on the substrate surface. This prototype substrate uses additional metal along the circumference of the substrate, which can degrade the quality of the FAF image. In other embodiments, the substrate can comprise relatively smaller and/or narrower metal boundary markers to improve image quality and/or to reduce inference or saturation of the image. Accordingly, other substrate embodiments can incorporate less metal to improve the quality of the FAF images. The width of a boundary marker can be from about 5 μm to about 500 μm. In an embodiment, smaller metal spatial markers may be incorporated into the substrate to define control regions. Anterior optics can also be utilized to improve cellular resolution FIG. 14 illustrates lipofuscin excitation and emission ranges.

Figure 15:
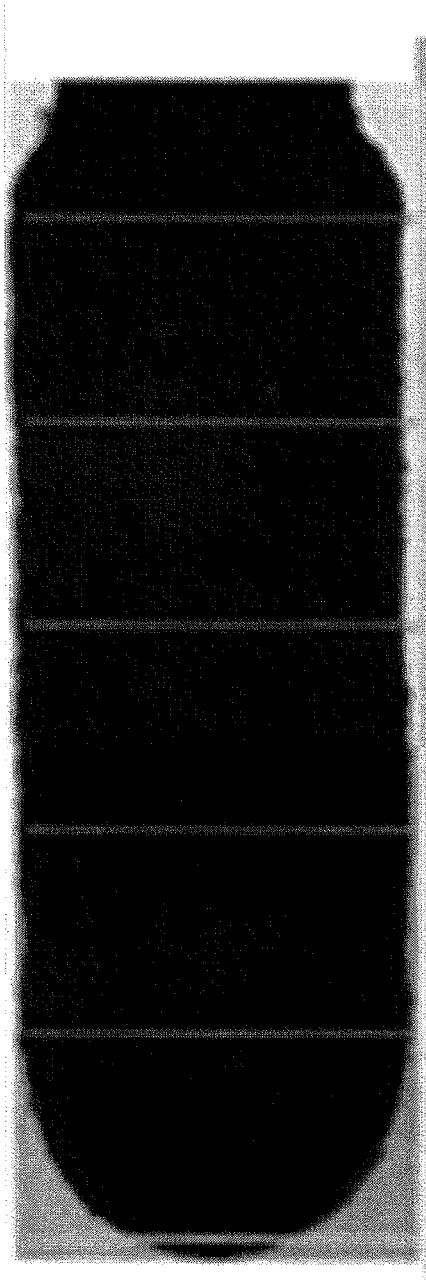
FIG. 15 illustrates a chart showing the results of cell counting along the width of six different regions of six substrates.

FIG. 15 illustrates a chart showing the results of cell counting along the width of six different regions of six substrates. In the illustrated chart, each substrate is marked with lines to assist cell counting. In the first substrate, a first region contains 23 cells, a second region contains 28 cells, a third region contains 30 cells, a fourth region contains 23 cells, and a fifth region contains 28 cells.

Computer System

Figure 16:
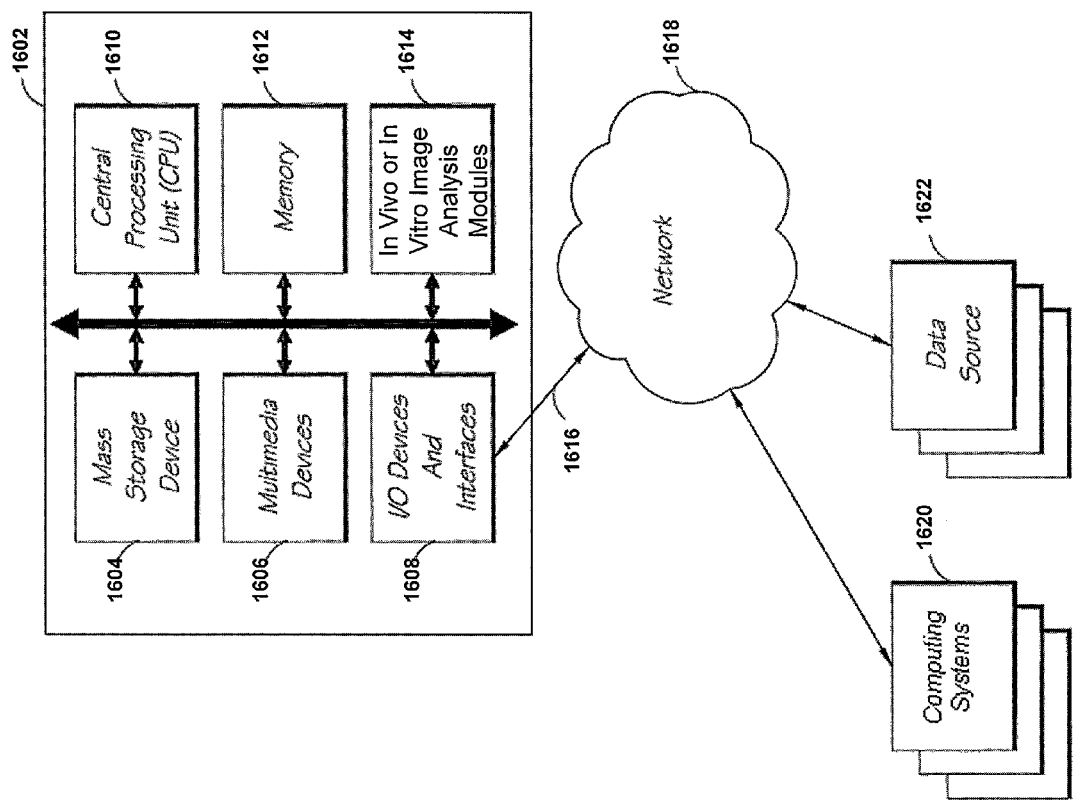
FIG. 16 is a block diagram depicting an embodiment of a computer hardware system configured to run software for implementing one or more embodiments of the in vitro substrate verification testing system and/or the in vivo substrate analysis system described herein.

In some embodiments, the systems, processes, and methods described above are implemented using a computing system, such as the one illustrated in FIG. 16. The example computer system 1602 is in communication with one or more computing systems 1620 and/or one or more data sources 1622 via one or more networks 1618. While FIG. 16 illustrates an embodiment of a computing system 1602, it is recognized that the functionality provided for in the components and modules of computer system 1602 may be combined into fewer components and modules, or further separated into additional components and modules.

In Vitro and/or In Vivo Image Analysis Module

The computer system 1602 includes an In Vitro and/or In Vivo Image Analysis Modules 1614 that carries out the functions, methods, acts, and/or processes described herein. The In Vitro and/or In Vivo Image Analysis Modules 1614 is executed on the computer system 1602 by a central processing unit 1610 discussed further below.

In general the word "module," as used herein, refers to logic embodied in hardware or firmware or to a collection of software instructions, having entry and exit points. Modules are written in a program language, such as JAVA, C or C++, or the like. Software modules may be compiled or linked into an executable program, installed in a dynamic link library, or may be written in an interpreted language such as BASIC letters, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems, and may be stored on or within any suitable computer readable medium, or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

Computing System Components

The computer system 1602 includes one or more processing units (CPU) 1610, which may include a microprocessor.

The computer system 1602 further includes a memory 1612, such as random access memory (RAM) for temporary storage of information, a read only memory (ROM) for permanent storage of information, and a mass storage device 1604, such as a hard drive, diskette, or optical media storage device. Alternatively, the mass storage device may be implemented in an array of servers. Typically, the components of the computer system 1602 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1602 includes one or more input/output (I/O) devices and interfaces 1608, such as a keyboard, mouse, touch pad, and printer. The I/O devices and interfaces 1608 can include one or more display devices, such as a monitor, that allows the visual presentation of data to a user. More particularly, a display device provides for the presentation of GUIs as application software data, and multi-media presentations, for example. The I/O devices and interfaces 1608 can also provide a communications interface to various external devices. The computer system 1602 may include one or more multi-media devices 1606, such as speakers, video cards, graphics accelerators, and microphones, for example.

Computing System Device/Operating System

The computer system 1602 may run on a variety of computing devices, such as a server, a Windows server, and Structure Query Language server, a Unix Server, a personal computer, a laptop computer, and so forth. In other embodiments, the computer system 1602 may run on a mainframe computer suitable for controlling and/or communicating with large databases, performing high volume transaction processing, and generating reports from large databases. The computing system 1602 is generally controlled and coordinated by an operating system software, such as z/OS, Windows 95, Windows 98, Windows NT, Windows 2000, Windows XP, Windows Vista, Windows 16, Linux, BSD, SunOS, Solaris, or other compatible operating systems, including proprietary operating systems. Operating systems control and schedule computer processes for execution, perform memory management, provide file system, networking, and I/O services, and provide a user interface, such as a graphical user interface (GUI), among other things.

Network

The computer system 1602 illustrated in FIG. 16 is coupled to a network 1618, such as a LAN, WAN, or the Internet via a communication link 1616 (wired, wireless, or a combination thereof). Network 1618 communicates with various computing devices and/or other electronic devices. Network 1618 is communicating with one or more computing systems 1620 and one or more data sources 1622. The In Vitro and/or In Vivo Image Analysis Module 1614 may access or may be accessed by computing systems 1620 and/or data sources 1622 through a web-enabled user access point. Connections may be a direct physical connection, a virtual connection, and other connection type. The web-enabled user access point may include a browser module that uses text, graphics, audio, video, and other media to present data and to allow interaction with data via the network 1618.

The output module may be implemented as a combination of an all-points addressable display such as a cathode ray tube (CRT), a liquid crystal display (LCD), a plasma display, or other types and/or combinations of displays. The output module may be implemented to communicate with input devices 1608 and they also include software with the appropriate interfaces which allow a user to access data through the use of stylized screen elements, such as menus, windows, dialogue boxes, tool bars, and controls (e.g., radio buttons, check boxes, sliding scales, and so forth). Furthermore, the output module may communicate with a set of input and output devices to receive signals from the user.

Other Systems

The computing system 1602 may include one or more internal and/or external data sources (e.g., data sources 1622). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

Additional Embodiments

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods may be carried out using any appropriate apparatus. Further, the disclosure herein of any particular feature, aspect, method, property, characteristic, quality, attribute, element, or the like in connection with an embodiment may be used in all other embodiments set forth herein. Thus, it is intended that the scope of the present invention herein disclosed should not be limited by the particular disclosed embodiments described above.

All of the methods and tasks described herein may be performed and fully automated by a computer system. The computer system may, in some cases, include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium. The various functions disclosed herein may be embodied in such program instructions, although some or all of the disclosed functions may alternatively be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid state memory chips and/or magnetic disks, into a different state.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Although the embodiments of the inventions have been disclosed in the context of a certain preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. For all of the embodiments described herein the steps of the methods need not be performed sequentially. Thus, it is intended that the scope of the present inventions herein disclosed should not be limited by the particular disclosed embodiments described above.

What is claimed is:

1. A computer-implemented method of analyzing in vivo an implanted substrate comprising stem cell-derived retinal pigment epithelium (RPE) cells, the method comprising:
   directing by a light source narrow-band light at the substrate;
   detecting by a detector fluorescence that is emitted from fluorophores coupled to the stem cell-derived RPE cells on the substrate;
   generating by a computer system a plurality of two-dimensional images of the substrate on an x-y plane at a plurality of focal depths along the z axis;
   combining by the computer system the plurality of two-dimensional images on the x-y plane to generate a single image;
   determining by the computer system a first number of stem cell-derived RPE cells in the single image;
   calculating by the computer system a first density of stem cell-derived RPE cells in the single image based on the determined first number of stem cell-derived RPE cells;
   comparing by the computer system the first number of stem cell-derived RPE cells and the first density of stem cell-derived RPE cells to a second number of stem cell-derived RPE cells and a second density of stem cell-derived RPE cells; and
   generating by the computer system a report based on the comparing,
   wherein the computer system comprises a computer processor and an electronic storage medium.

2. The computer-implemented method of claim 1, wherein the second number of stem cell-derived RPE cells and the second density of stem cell-derived RPE cells are determined from the same substrate at a second point in time.

3. The computer-implemented method of claim 1 further comprising identifying double counting of stem cell-derived RPE cells by the computer system by identifying in-focused objects occurring at a same x-y coordinate and occurring at different focal depths along a z axis.

4. The computer-implemented method of claim 1 further comprising employing statistical techniques to approximate a number of cells in non-imaged regions of the substrate.

5. The computer-implemented method of claim 1, wherein the narrow-band light source has a wavelength of about 488 nm.

6. The computer-implemented method of claim 1, wherein the narrow-band light source has a wavelength of about 450 nm to about 800 nm.

7. The computer-implemented method of claim 1, wherein the substrate further comprises markings configured to assist counting a number of stem cell-derived RPE cells.

8. The computer-implemented method of claim 1 further comprising determining a level of interdigitation between stem cell-derived RPE cells on the substrate and photoreceptors.

9. The computer-implemented method of claim 1 further comprising determining a degree of pigmentation of stem cell-derived RPE cells on the substrate, wherein the determining the degree of pigmentation further comprises:
   directing a first light source at the substrate, wherein the first light source has a wavelength within a range that lipofuscin fluoresces but not melanopsin;
   generating by the computer system a first image of the substrate from fluorescence reemitted after directing the first light source;
   counting by the computer system a first number of stem cell-derived RPE cells in the first image;
   directing a second light source at the substrate, wherein the second light source has a wavelength within a range that melanopsin fluoresces but not lipofuscin;
   generating by the computer system a second image of the substrate from fluorescence reemitted after directing the second light source;
   counting by the computer system a second number of stem cell-derived RPE cells in the second image; and
   comparing by the computer system the first number of stem cell-derived RPE cells to the second number of stem cell-derived RPE cells.

10. The computer-implemented method of claim 1 further comprising determining a degree of spatial separation between the substrate and stem cell-derived RPE cells on the substrate.

11. The computer-implemented method of claim 1, wherein the substrate further comprises a boundary marker located along edges of the substrate.

12. The computer-implemented method of claim 11, wherein a width of the boundary marker is within a range from about 5 μm to about 500 μm.

13. The computer-implemented method of claim 1 further comprising using photoacoustic imaging to detect a presence of stem cell-derived RPE cells on the substrate.

14. The computer-implemented method of claim 1 further comprising collecting indirect structural information of photoreceptors within the eye by a reflectometer to assess implantation of stem cell-derived RPE cells, wherein the reflectometer is configured to monitor rhodopsin pigment in the photoreceptors.

15. The computer-implemented method of claim 1 further comprising collecting indirect structural information of photoreceptors within the eye by adaptive optics with or without a scanning laser opthalmoscope.

16. The computer-implemented method of claim 1, wherein the computer system comprises one or more computer systems.

* * * * *